US009533007B2

(12) United States Patent
Reed et al.

(10) Patent No.: US 9,533,007 B2
(45) Date of Patent: Jan. 3, 2017

(54) NANOCERIA FOR THE TREATMENT OF OXIDATIVE STRESS

(71) Applicant: Cerion, LLC, Rochester, NY (US)

(72) Inventors: Kenneth Joseph Reed, Brighton, NY (US); Wendi Ann Costanzo, Webster, NY (US); Joseph Samuel Erlichman, Canton, NY (US); Eric Leslie Bell, Webster, NY (US)

(73) Assignee: CERION, LLC, Rochester, NY (US)

( * ) Notice: Subject to any disclaimer, the term of this patent is extended or adjusted under 35 U.S.C. 154(b) by 0 days.

(21) Appl. No.: 14/690,781

(22) Filed: Apr. 20, 2015

(65) Prior Publication Data

US 2015/0231174 A1    Aug. 20, 2015

Related U.S. Application Data

(62) Division of application No. 13/836,827, filed on Mar. 15, 2013, now Pat. No. 9,034,392.

(60) Provisional application No. 61/689,806, filed on Jun. 13, 2012, provisional application No. 61/690,100, filed on Jun. 18, 2012, provisional application No.
(Continued)

(51) Int. Cl.
| | |
|---|---|
| *A61K 9/16* | (2006.01) |
| *A61K 33/24* | (2006.01) |
| *A61K 9/10* | (2006.01) |
| *B82Y 5/00* | (2011.01) |
| *B01J 13/02* | (2006.01) |

(52) U.S. Cl.
CPC .................. *A61K 33/24* (2013.01); *A61K 9/10* (2013.01); *A61K 9/16* (2013.01); *A61K 9/1694* (2013.01); *B01J 13/02* (2013.01); *B82Y 5/00* (2013.01); *C01P 2004/64* (2013.01)

(58) Field of Classification Search
CPC .......... A61K 9/1694; B01J 13/02; B82Y 5/00; C01P 2004/64
See application file for complete search history.

(56) References Cited

U.S. PATENT DOCUMENTS

| 6,530,968 B2 | 3/2003 | Tsuchiya |
| 7,534,453 B1 | 5/2009 | Rzigalinski |
| 2003/0082237 A1 | 5/2003 | Cha |

(Continued)

FOREIGN PATENT DOCUMENTS

| CN | 101683999 | 3/2010 |
| EP | 2064153 | 6/2009 |

(Continued)

OTHER PUBLICATIONS

Office Action mailed Jul. 23, 2015 in U.S. Appl. No. 13/864,620.
(Continued)

*Primary Examiner* — Carlos Azpuru
(74) *Attorney, Agent, or Firm* — RatnerPrestia

(57) ABSTRACT

A process for making nanoparticles of biocompatible materials is described, wherein an aqueous reaction mixture comprising cerous ion, citric acid and ethylenediaminetetraacetic acid in a predetermined ratio, an oxidant, and water is provided along with temperature conditions to directly form, without isolation, a stable dispersion of cerium oxide nanoparticles. These biocompatible cerium oxide nanoparticles may be used to prevent and/or treat oxidative stress related diseases, such as stroke, relapse/remitting multiple sclerosis, chronic-progressive multiple sclerosis, amyotrophic lateral sclerosis, and ischemic reperfusion injury.

10 Claims, 35 Drawing Sheets

Related U.S. Application Data

61/795,241, filed on Oct. 12, 2012, provisional application No. 61/796,639, filed on Nov. 16, 2012.

(56) References Cited

U.S. PATENT DOCUMENTS

| | | | |
|---|---|---|---|
| 2003/0187077 | A1 | 10/2003 | Chane-Ching |
| 2006/0018851 | A1 | 1/2006 | Patt |
| 2010/0152077 | A1 | 6/2010 | Allston |
| 2010/0221334 | A1 | 9/2010 | Fink |
| 2010/0308258 | A1 | 12/2010 | Kroell |

FOREIGN PATENT DOCUMENTS

| | | |
|---|---|---|
| WO | 2007002662 | 1/2007 |
| WO | 2008002323 | 1/2008 |
| WO | 2008030805 | 3/2008 |
| WO | 2008030815 | 3/2008 |

OTHER PUBLICATIONS

Zhang et al., "Synthesis and Characterization of Mesoporous Ceria with Hierarchical Nanoarchitecture Controlled by Amino Acids," Journal of Physical Chemistry B, 2006, vol. 110, No. 51, pp. 25782-25790.

Aryal et a., "Study of Electrolyte Induced Aggregation of Gold Nanoparticles Capped by Amino Acids," Journal of Colloid and Interface Science, 2006, vol. 299, pp. 191-197.

Nitric Acid Material Data Sheet, CF Industries Sales, LLC, 2012, 8 pages.

Notice of Allowance mailed Dec. 3, 2015 for U.S. Appl. No. 13/864,620.

"Aliphatic Amino Acids," The Biology Project, 2004. downloaded from http://www.biology.arizona.edu/biochemistry/problem_sets/aa/aliphatic/html on Feb. 18, 2014.

Entire Prosecution History for U.S. Appl. No. 13/836,827, filed March 15, 2013, Entittled "Nanoceria for the Treatment of Oxidative Stress".

Entire Prosecution History for U.S. Appl. No. 13/864,620, filed April 17, 2013, Entittled "Nanoparticles of Cerium and Amino Acids".

Estevez, A.Y. et al., "Neuroprotective Mechanisms of Cerium Oxide Nanoparticles in a Mouse Hippocampal Brain Slice Model of Ischemia," Free Radic. Biol. Med, 2011, doi:10.1016/j.freeradbiomed.2011.06.006.

Forrestier, Gilles, Authorized Officer of EPO; International Search Report of PCT/US2013/036943; Oct. 11, 2013.

Garrett, "Some Common Cyrstal Structures," 1998.

Hardas, Sarita et al., "Brain Distribution and Toxicological Evaluation of a Systemically Delivered Engineered Nanoscale Ceria," Toxicologial Sciences 116(2), pp. 562-576, 2010.

Hohmann, Birgit, Authorized Officer, EPO, International Search Report of PCT/US2013/032318, Jun. 5, 2013.

Illustrated Glossary of Organic Chemistry, downloaded from http://www.chem.ucla.edu/harding/IGOC/A/amino_acid/html on Feb. 18, 2014.

Karokoti, A.S. et al., "Nanoceria as Antioxidant: Systhesis and Biomedical Applications," Journal of the Minerals, Metals & Materials Society (JOM), 60(2), pp. 33-37, Mar. 2008.

Karokoti, A.S. et al.; "Direct Synthesis of Nanoceria in Aqueous Polyhydroxyl Solutions," J. Physical Chem. C 111, pp. 17232-17240, 2007.

Kim, Chi Kyung et al., "Ceria Nanoparticles That Can Protect Against Ischemic Stroke" , Angew. Chem. Int., vol. 6, pp. 1-6, ED. 2012.

Masui, T. et al., "Synthesis of Cerium Oxide Nanoparticles by Hydrothermal Crystallization With Citric Acid," J. Mater. Sci. Lett. 21, pp. 489-491, 2002.

Material Safety and Data Sheet for Ethylenediaminetetraacetic acid from Sigma Aldrich, 2014.

Robert A. Yokel et al. "Biodistribution and Oxidative Stress Effects of a Systemically-Introduced Commercial Ceria Engineered Nanomaterial," Nanotoxicology, vol. 3, pp. 234-248, Sep. 2009.

Rzigalinski, Beverly A. PH.D., "Nanoparticles and Cell Longevity," Technology in Cancer Research and Treatment, vol. 4, No. 6, pp. 651-659, Dec. 2005.

"Metallic Nanocrystallites and Their Interaction With Microbial Systems" ; Springer, XP002697256, Mar. 2, 2012.

Chinese Office Action dated May 26, 2016 for Chinese Application No. 201380030839.3, including English translation, 23 pages.

S-A = Signma-Aldrich
AA 1:14 = Alfa Aesar Ce-Citrate ratio 1:14
AA 1:9 = Alfa Aesar Ce-Citrate Ratio 1:9

NANOCERIA FOR THE TREATMENT OF OXIDATIVE STRESS

CROSS-REFERENCE TO RELATED APPLICATIONS

This application is a Divisional Application of U.S. patent application Ser. No. 13/836,827, filed Mar. 15, 2013, which itself claims priority to Provisional Application Ser. No. 61/689,806, NANOCERIA FOR THE TREATMENT OF MULTIPLE SCLEROSIS, filed Jun. 13, 2012, Provisional Application Ser. No. 61/690,100, NANOCERIA FOR THE PREVENTION AND TREATMENT OF MULTIPLE SCLEROSIS, filed Jun. 18, 2012, Provisional Application Ser. No. 61/795,241, BIOLOGICAL EFFECTS OF NANOCERIA IN A MODEL OF MULTIPLE SCLEROSIS, filed Oct. 12, 2012, and Provisional Application Ser. No. 61/796,639, NANOCERIA FOR THE REDUCTION OF OXIDATIVE STRESS, filed Nov. 16, 2012, the disclosures of all of these applications are incorporated herein by reference in their entirety.

FIELD OF THE INVENTION

The present invention relates in general to improvements in the field of nanomedicine. In particular, the invention relates to cerium-containing nanoparticles prepared with biocompatible materials, to methods of preparing such nanoparticles, and to the use of such nanoparticles to prevent and to treat inflammation and oxidative stress related events and diseases.

BACKGROUND OF THE INVENTION

Free radical oxidative stress plays a major role in the pathogenesis of many human diseases, and in particular, neurodegenerative diseases. Treatment with antioxidants, which may reduce particular free radical species, therefore, might theoretically prevent tissue damage and improve both survival and neurological outcome. Free radicals in physiological environments can often be classified as either a reactive oxygen species (ROS) or a reactive nitrogen species (RNS). Free radicals are highly reactive chemical species and readily react with proteins, lipids and nucleic acids at a subcellular level and thereby contribute to the progression of various diseases.

The origin of the use of nanoceria in nanomedicine can be traced to the seminal work of Bailey and Rzigalinski, wherein the application of ultrafine cerium oxide particles to brain cells in culture was observed to greatly enhanced cell survivability, as described by Rzigalinski in Nanoparticles and Cell Longevity, Technology in Cancer Research & Treatment 4(6), 651-659 (2005). More particularly, rat brain cell cultures in vitro were shown to survive approximately 3-4 times longer when treated with 2-10 nanometer (nm) sized cerium oxide nanoparticles synthesized by a reverse micelle micro emulsion technique, as reported by Rzigalinski et al. in U.S. Pat. No. 7,534,453, filed Sep. 4, 2003. Cultured brain cells exposed to a lethal dose of free radicals generated by hydrogen peroxide or ultraviolet light exposures were afforded considerable protection by the cerium oxide nanoparticles. In addition, the cerium oxide nanoparticles were reported to be relatively inert in the murine body, with low toxicity (e.g. tail vein injections produced no toxic effects). While no in vivo medical benefits were reported, benefits were postulated for treatments with these ceria nanoparticles, including reduced inflammation associated with wounds, implants, arthritis, joint disease, vascular disease, tissue aging, stroke and traumatic brain injury.

However, a host of problems with these particular nanoceria particles was subsequently reported by Rzigalinski et al. in WO 2007/002662. Nanoceria produced by this reverse micelle micro emulsion technique suffered from several problems: (1) particle size was not well-controlled within the reported 2-10 nanometer (nm) range, making variability between batches high; (2) tailing (carryover contamination) of surfactants, such as sodium bis(ethylhexyl)sulphosuccinate, also known as docusate sodium or (AOT), used in the process into the final product, caused toxic responses; (3) inability to control the amount of surfactant tailing posed problems with agglomeration when these nanoparticles were placed in biological media, resulting in reduced efficacy and deliverability; and (4) instability of the valence state of cerium (+3/+4) over time. Thus, the cerium oxide nanoparticles produced by the reverse micelle micro emulsion technique were highly variable from batch to batch, and showed higher than desired toxicity to mammalian cells.

As an alternative, Rzigalinski et al. in WO 2007/002662 reported the biological efficacy of nanoceria synthesized by high temperature techniques, obtained from at least three commercial sources. These new sources of cerium oxide nanoparticles were reported to provide superior reproducibility of activity from batch to batch. It was further reported that, regardless of source, cerium oxide particles having a small size, narrow size distribution, and low agglomeration rate are most advantageous. In regard to size, this disclosure specifically asserts that in embodiments where particles are taken into the interior of cells, the preferable size range of particles that are taken into the cell are from about 11 nm to about 50 nm, such as about 20 nm. In embodiments where particles exert their effects on cells from outside the cells, the preferable size range of these extracellular particles is from about 11 nm to about 500 nm.

Rzigalinski et al. also report that for delivery, the nanoparticles were advantageously in a non-agglomerated form. To accomplish this, they reported that stock solutions of about 10% by weight could be sonicated in ultra-high purity water or in normal saline prepared with ultra-high purity water. However, as others have noted, sonicated aqueous dispersions of nanoceria synthesized by high temperature techniques (e.g. obtained from commercial sources) are highly unstable, and settle rapidly (i.e. within minutes), causing substantial variability in administering aqueous dispersions of nanoceria derived from these sources.

Rzigalinski et al. report biological efficacy in relatively simple model systems, including in vitro cell cultures, orally fed *Drosophila melanogaster* fruit flies, and in mice that were tail vein injected with an apparently less than therapeutic dose (300 nanomoles or about 0.2 mg/kg).

Yokel et al. in Nanotoxicology, 2009, 3(3): 234-248, describe an extensive study of the biodistribution and oxidative stress effects of a commercial ceria nanomaterial. In particular, a 5% nanoceria dispersion obtained from Aldrich (#639648) was sonicated for 3 minutes and infused into rats at 50, 250 and 750 mg/kg nanoceria dose. The nature of any nanoparticle surface stabilizer(s) was unknown for this material. The size of the nanoceria particles was characterized by a variety of techniques and reported to be on average 31+/−4 nm by dynamic light scattering. Transmission electron microscopy (TEM) revealed that most of the particles were platelets with a bimodal size distribution with peaks at 8 nm and 24 nm, along with some particles ~100 nm. It was observed that blood incubated for 1 hour with this form of nanoceria had agglomerates ranging from ~200 nm to greater than 1 micron, and that when infused into rats, it was rapidly cleared from the blood (half-life of 7.5 minutes). Most of the nanoceria was observed to accumulate in the liver and spleen, while it was not clear that any substantial amount had penetrated the blood brain barrier and entered brain tissue cells.

Yokel et al. then sought precise control over the nanoceria surface coating (stabilizer) and prepared stable aqueous dispersions of nanoceria by the direct two-step hydrothermal preparation of Masui et al., 3. Mater. Sci. Lett. 21, 489-491 (2002), which included sodium citrate as a biocompatible stabilizer. High resolution TEM revealed that this form of nanoceria possessed crystalline polyhedral particle morphology with sharp edges and a narrow size distribution of 4-6 nm. Citrate stabilized dispersions of these 5 nm average size ceria nanoparticles were reported to be stable for more than 2 months at a physiological pH of 7.35 and zeta potential of −53 mV. Thus no sonication prior to administration was required.

Results of an extensive biodistribution and toxicology study of this form of citrate stabilized nanoceria were reported by Hardas et al., Toxicological Sciences 116(2), 562-576 (2010). Surprisingly, they report that compared with the previously studied ~30 nm nanoceria (Aldrich (#639648), described above), this smaller nanoceria was more toxic, was not seen in the brain, and produced little effect on oxidative stress in the hippocampus and cerebellum. The results were contrary to the hypothesis that smaller engineered nanomaterial would readily permeate the blood brain barrier.

While cerium oxide containing nanoparticles can be prepared by a variety of techniques known in the art, the particles typically require a stabilizer to prevent undesirable agglomeration. In regard to biocompatible nanoceria stabilizers used previously, Masui et al., J. Mater. Sci. Lett. 21, 489-491 (2002) describe a two-step hydrothermal process that directly produces stable aqueous dispersions of ceria nanoparticles that uses citrate buffer as a stabilizer. However, this process is both time consuming and equipment intensive, requiring two separate 24 hours reaction steps in heavy closed-reactors.

Sandford et al., WO 2008/002323 A2, report an aqueous preparation technique using a biocompatible stabilizer (acetic acid) that directly produces nanoparticle dispersions of cerium dioxide without a precipitation or isolation step, and without subsequent calcination. Cerous ion is slowly oxidized to ceric ion by nitrate ion, and a stable non-agglomerated sol of 11 nm crystallite size (and approximately equal grain size) is obtained when acetic acid is used as a stabilizer.

DiFrancesco et al. in PCT/US2007/077545, METHOD OF PREPARING CERIUM DIOXIDE NANOPARTICLES, filed Sep. 4, 2007, describes the oxidation of cerous ion by hydrogen peroxide at low pH (<4.5) in the presence of biocompatible stabilizers, such as citric acid, lactic acid, tartaric acid, ethylenediaminetetraacetic acid (EDTA), and combinations thereof. Specifically, the stabilizer lactic acid and the combination of lactic acid and EDTA are shown to directly produce stable dispersions of nanoceria (average particle size in the range of 3-8 nm), without an intermediate particle isolation step.

Karakoti et al. in J. Phys. Chem. C 111, 17232-17240 (2007) report a direct synthesis of nanoceria in mono/polysaccharides by oxidation of cerous ion in both acidic conditions (by hydrogen peroxide) and basic conditions (by ammonium hydroxide). The specific biocompatible stabilizers disclosed include glucose and dextran. Individual particle sizes as small as 3-5 nm are disclosed, however, weak agglomerates of 10-30 nm result. While the source of the colloidal instability is not described, it is believed that the magnitude of the zeta potential of these particles may not have been sufficiently large.

Karakoti et al. in JOM (Journal of the Minerals, Metals & Materials Society) 60(3), 33-37 (2008) comment on the challenge of synthesizing stable dispersions of nanoceria in biologically relevant media, so as to be compatible with organism physiology, as requiring an understanding of colloidal chemistry (zeta potential, particle size, dispersant, pH of solution, etc.) so as not to interfere with the reduction/oxidation (redox) ability of the nanoceria that enables the scavenging of free radicals (reactive oxygen species (ROS) and reactive nitrogen species). Karakoti et al. specifically describe the oxidation of cerium nitrate by hydrogen peroxide at low pH (<3.5) in the absence of any stabilizer, as well as, in the presence of dextran, ethylene glycol and polyethylene glycol (PEG) stabilizers. Particle sizes of 3-5 nm are reported, although particle agglomeration to 10-20 nm is also reported.

Kim et al. in Angew. Chem. Int. Ed. 2012, 51, 1-6 report that 3 nm nanoceria synthesized by a reverse micelle method and encapsulated with phospholipid-polyethylene glycol (PEG) can protect against ischemic stroke in rats by reducing brain infarct volume and by scavenging ROS. However, higher doses are not protective, and it is believed that this may be related to surfactant tailing problems, as noted above, that plague the reverse micelle synthesis method.

There remains a need for efficient and effective methods and agents for mediating and ameliorating damage from free radical oxidative stress. In addition, a need remains for further improvements in methods for the direct preparation (i.e. without a particle isolation step) of biocompatible dispersions of cerium-containing nanoparticles, for example, in higher yield, in a shorter period of time and at higher suspension densities, that are sufficiently small in size, capable of penetrating a healthy or unhealthy blood brain barrier, more uniform in size frequency distribution, stable and non-toxic in a wide range of biological media, with increased cellular uptake and vascular circulation time in vivo. Additionally, it would be quite useful to produce medicaments for the prevention and/or treatment of inflammation and oxidative stress related events, such as ischemic stroke and reperfusion injury, and oxidative stress related diseases, in particular, central nervous system diseases, such as multiple sclerosis and amyotrophic lateral sclerosis, in mammals, and particularly in humans.

SUMMARY OF THE INVENTION

In accordance with one aspect of the invention, a method of making a dispersion of nanoparticles is provided, comprising: forming a reaction mixture comprising cerous ion, citric acid (CA) and ethylenediaminetetraacetic acid (EDTA) in a molar ratio (CA/EDTA) ranging from about 3.0 to about 0.1 (i.e. from about 3:1 to about 1:9), an oxidant, and water; optionally, heating or cooling the reaction mixture, and directly forming, without isolation, a dispersion of cerium-containing nanoparticles.

In a second aspect of the invention, a process of preventing (i.e. prophylactically treating) an oxidative stress related disease, and in particular, a central nervous system disease, such as multiple sclerosis or amyotrophic lateral sclerosis, comprising administering, prior to the onset of an oxidative stress related disease, an effective amount of a cerium-containing nanoparticle prepared in the presence a mixture of citric acid and ethylenediaminetetraacetic acid in a molar ratio ranging from about 3.0 to about 0.1, is provided.

In a third aspect of the invention, a process of treating an oxidative stress related event or disease, and in particular, a central nervous system disease, such as multiple sclerosis or amyotrophic lateral sclerosis, comprising administering, after onset of a disease or event, an effective amount of cerium-containing nanoparticles prepared in the presence a mixture of citric acid and ethylenediaminetetraacetic acid in a molar ratio ranging from about 3.0 to about 0.1, is provided.

In a fourth aspect of the invention, a nanoparticle comprising cerium oxide, citric acid and ethylenediaminetetraacetic acid is provided, wherein the molar ratio of citric acid and ethylenediaminetetraacetic acid added during preparation is in a range of about 3.0 to about 0.1.

In a fifth aspect of the invention, a nanoparticle comprising cerium oxide, citric acid and ethylenediaminetetraacetic acid, wherein the molar ratio of citric acid to ethylenediaminetetraacetic acid ranges from about 3.0 to about 0.1, is provided.

In a sixth aspect of the invention, a pharmaceutical composition for the prevention and/or treatment of an oxidative stress related event or disease, comprises a cerium oxide nanoparticle, wherein the molar ratio of citric acid and ethylenediaminetetraacetic acid added during preparation is in a range of about 3.0 to about 0.1, is provided.

In a seventh aspect of the invention, a pharmaceutical composition for the prevention and/or treatment of an oxidative stress related disease, comprises a cerium oxide nanoparticle capable of penetrating a mammalian blood brain barrier, is provided.

DETAILED DESCRIPTION OF THE INVENTION

Figure 1:
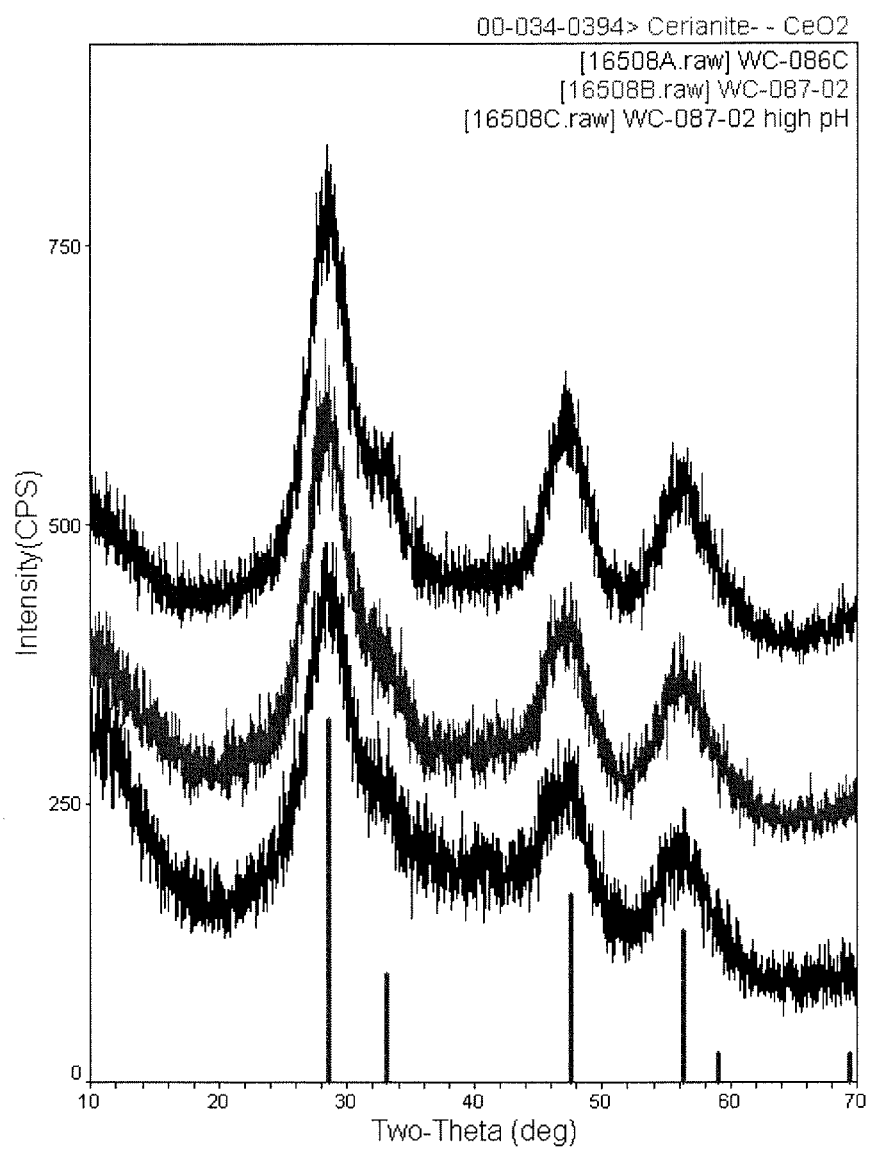
FIG. 1 contains powder X-ray diffraction (XRD) spectra of CA/EDTA ceria nanoparticles along with the line spectrum of CeO2 (Cerianite).

It is to be understood that elements not specifically shown or described may take various forms well known to those skilled in the art. The invention is defined by the claims.

As used herein, the term nanoparticle includes particles having a mean diameter of less than 100 nm. For the purposes of this disclosure, unless otherwise stated, the diameter of a nanoparticle refers to its hydrodynamic diameter, which is the diameter determined by dynamic light scattering technique and includes molecular adsorbates and the accompanying solvation shell of the particle. Alternatively, the geometric particle diameter can be estimated by analysis of transmission electron micrographs (TEM).

As used herein, various cerium-containing materials are interchangeably described as "ceria", "cerium oxide" or "cerium dioxide." It will be understood by one skilled in the chemical arts, that the actual oxidic anions present in these materials may comprise oxide anions or hydroxide anions, or mixtures thereof, such as hydrated oxide phases (e.g. oxyhydroxide). In addition, it is known that compositions of matter may be comprised of solid solutions of multivalent cations, and are termed non-stoichiometric solids. Thus, for oxide phases comprised of metal cations of multiple oxidation states, it is understood that the total amount of oxidic anions present will be determined by the specific amounts of the various oxidation states of the metal cations present (e.g. $Ce^{3+}$ and $Ce^{4+}$), such that charge neutrality is maintained. For non-stoichiometric phases nominally described as metal dioxides, this is embodied in the chemical formula $MO_{2-\delta}$ wherein the value of $\delta$ (delta) may vary. For cerium oxides, $CeO_{2-\delta}$, the value of $\delta$ (delta) typically ranges from about 0.0 to about 0.5, the former denoting cerium (IV) oxide, $CeO_2$, the latter denoting cerium (III) oxide, $CeO_{1.5}$ (alternatively denoted $Ce_2O_3$). Alternatively, the value of $\delta$ (delta) denotes the amount of oxygen vacancies present relative to cerium (IV) oxide ($CeO_2$). For each oxygen di-anion vacancy present, two cerous ions ($Ce^{3+}$) are present, to preserve charge neutrality.

In one embodiment of the invention, a process is provided comprising: forming a reaction mixture comprising cerous ion, citric acid, ethylenediaminetetraacetic acid (EDTA), an oxidant, and water; optionally heating or cooling the reaction mixture; and directly forming, without isolation, a stable dispersion of nanoparticles.

In various embodiments, the molar ratio of citric acid to EDTA in the reaction mixture ranges from about 3:1 to about 1:9; from about 3:1 to about 2:1; and from about 1.2:1.0 to about 1:9.

In various embodiments, the oxidant includes molecular oxygen or air, or compounds more oxidizing than molecular oxygen (or an ambient atmosphere of air). In other embodiments, the oxidant has an aqueous half-cell reduction potential greater than −0.13 volts relative to the standard hydrogen electrode. In particular embodiments the oxidant is an alkali metal or ammonium perchlorate, chlorate, hypochlorite or persulfate; ozone, a peroxide or a combination thereof. In a particular embodiment, a two-electron oxidant, such as hydrogen peroxide, is used. In particular embodiments, hydrogen peroxide is present in an amount greater than one-half the molar amount of cerous ion. In still other embodiments, the amount of oxidant present varies widely in relation to the amount of cerium ions or other metal ions present.

In a particular embodiment, molecular oxygen is passed through the reaction mixture.

In particular embodiments, the temperature of the reaction mixture is greater than or less than ambient temperature. In particular embodiments, the reaction mixture is heated or cooled to temperatures greater than or less than ambient temperature. In various embodiments, the reaction mixture is heated or cooled to temperatures greater than about 30° C., greater than about 40° C., greater than about 50° C., greater than about 60° C., greater than about 70° C., greater than about 80° C. or greater than about 90° C. In a particular embodiment, the reaction mixture is heated or cooled to a temperature less than the boiling temperature of water.

In various embodiments, the nanoparticles formed are amorphous, semi-crystalline or substantially crystalline, or crystalline. In a particular embodiment the nanoparticles formed are characterized by a cubic fluorite crystal structure. In a particular embodiment, the nanoparticles formed are characterized by a cerium oxide crystal structure.

As used herein, the terms semi-crystalline and substantially crystalline refer to nanoparticles that have at least some crystalline structure. As one of ordinary skill in the art recognizes, accurate characterization of particles becomes increasingly difficult as the particle size becomes smaller because smaller particles have less detectable long-range order.

In at least one embodiment, the nanoparticles are crystalline and may be monocrystalline or polycrystalline.

In particular embodiments, the crystallinity of the nanoparticles formed is enhanced by heating of the reaction mixture.

In particular embodiments, the nanoparticles formed are dehydrated or dehydroxylated by heating of the reaction mixture.

In various embodiments, the nanoparticles formed have a hydrodynamic diameter less than 100 nm, less than 80 nm, less than 60 nm, less than 40 nm, less than 20 nm, less than 10 nm, less than 5.0 nm, less than about 3 nm or less than about 2.0 nm.

In a particular embodiment, the nanoparticles formed have a geometric diameter less than the hydrodynamic diameter.

In various embodiments, the nanoparticles formed have a coefficient of variation (COV) of the particle size, defined as the standard deviation of the particle size divided by the average particle size, less than about 15%, less than about 10%, less than about 5%, or less than about 3%.

In a particular embodiment, a nanoparticle comprising cerium is provided. In other embodiments, nanoparticles comprising a cerium oxide, a cerium hydroxide or a cerium oxyhydroxide are provided.

In a particular embodiment, a nanoparticle comprising citric acid, ethylenediaminetetraacetic acid and a cerium oxide, cerium hydroxide or cerium oxyhydroxide, is provided.

In other embodiments, a nanoparticle having a zeta potential less than or equal to zero is provided. In particular embodiments, a nanoparticle comprising cerium oxide, citric acid, ethylenediaminetetraacetic acid and having a zeta potential less than or equal to zero is provided. In particular embodiments, a nanoparticle comprising cerium oxide, citric acid, ethylenediaminetetraacetic acid, and having a zeta potential less than −10 mV, less than −20 mV, less than −30 mV, less than −40 mV or less than about −50 mV, is provided. In particular embodiments, a nanoparticle comprising cerium oxide, citric acid, ethylenediaminetetraacetic acid, and having a zeta potential in the range of −15 mV to −30 mV, is provided.

In particular embodiments, a nanoparticle having a zeta potential greater than zero is provided. In particular embodiments, a nanoparticle comprising cerium, citric acid, ethylenediaminetetraacetic acid, and having a zeta potential greater than zero, greater than 10 mV, greater than 20 mV, greater than 30 mV, greater than 40 mV or greater than 50 mV, is provided.

In various embodiments, the zeta potential of the nanoparticle is altered by adjusting the pH, the citric acid and/or ethylenediaminetetraacetic acid content, or a combination thereof, of the nanoparticle dispersion.

In a particular embodiment, the zeta potential of the nanoparticle is altered by adjusting the citric acid and ethylenediaminetetraacetic acid content of the nanoparticle dispersion to less than saturation coverage.

In another embodiment, the zeta potential of the nanoparticle is altered by adjusting both the pH of the nanoparticle dispersion, and the citric acid and ethylenediaminetetraacetic acid content to less than saturation coverage.

In various embodiments, the dispersion of cerium-containing nanoparticles contains substantially non-agglomerated nanoparticles, greater than 90 percent non-agglomerated nanoparticles, greater than 95 percent non-agglomerated nanoparticles, greater than 98 percent non-agglomerated nanoparticles, and entirely non-agglomerated nanoparticles.

In a particular embodiment, the non-agglomerated nanoparticles are crystalline, and are alternatively referred to as single particle crystallites or individual crystallites.

In a particular embodiment, the nanoparticle dispersion formed is washed to remove excess ions or by-product salts. In various embodiments, the nanoparticle dispersion is washed such that the ionic conductivity is reduced to less than about 15 millisiemens per centimeter (mS/cm), less than about 10 mS/cm, less than about 5 mS/cm or less than about 3 mS/cm. In particular embodiments, the nanoparticle dispersion formed is washed by dialysis, diafiltration or centrifugation.

In particular embodiments, the nanoparticle dispersions formed are concentrated to remove excess solvent or excess water. In particular embodiments, the nanoparticle dispersion is concentrated by dialysis, diafiltration or centrifugation.

In various embodiments, the concentration of nanoparticles in the dispersion is greater than about 0.05 molal, greater than about 0.5 molal or greater than about 2.0 molal (approximately 35% solids in a given dispersion).

In particular embodiments, the size distributions of the nanoparticles are substantially monomodal. In other embodiments, the nanoparticle size has a coefficient of variation (COV) less than about 30%, less than about 25%, less than about 20%, less than about 15%, less than about 10% or less than about 5%, where the COV is defined as the standard deviation divided by the mean.

In particular embodiments, various mixing devices known in the art are employed to stir, mix, shear or agitate the contents of the reaction mixture. In various embodiments, mixers comprising stir bars, marine blade propellers, pitch blade turbines or flat blade turbines are used. In a particular embodiment, a high shear mixer that forces the reaction mixture to pass through a screen comprising holes ranging in size from fractions of a millimeter to several millimeters, is employed. In particular embodiments, a colloid mill or a Silverson® High Shear Mixer is employed. In particular embodiments, one or more of the reactants is introduced below the surface of the aqueous reaction mixture. In a particular embodiment, a reactant is introduced below the surface of the aqueous reaction mixture in close proximity to a mixing device.

In one embodiment of the invention, a process of solvent shifting the aqueous nanoparticle dispersion to a less polar solvent composition by methods disclosed in commonly assigned US Patent Application Publication 2010/0152077, is employed. In a specific embodiment, the nanoparticle dispersion is passed through a diafiltration column with an organic diluent comprising, for example, an alcohol or a glycol ether.

In at least one embodiment, the dispersion of cerium-containing nanoparticles is stable for at least 2 months, such as, for example, at least 12 months.

Without being bound by any theory, the proposed use of cerium oxides for the treatment of inflammation and oxidative stress related diseases (e.g. ROS mediated diseases) is based in part upon a belief that cerium oxides may function as catalytic scavengers of free radicals. The existence of and facile inter-conversion of cerium in a mixture of $Ce^{3+}$ and $Ce^{4+}$ valence states may enable cerium oxides to reduce and/or oxidize free radicals to less harmful species in a catalytic or auto-regenerative manner. Redox reactions may occur on the surface of cerium oxide nanoparticles (CeNPs) that neutralize tissue-damaging free radicals. For example, it is believed to be desirable to oxidize superoxide anion ($O^{2-}$) to molecular oxygen, to oxidize peroxynitrite anion (ONOO$^-$) to physiologically benign species, and to reduce hydroxyl radical (.OH) to hydroxide anion. This may in turn enable a greatly reduced dosing regimen in comparison to, for example, sacrificial antioxidants currently available to treat oxidative stress related diseases and events.

In particular embodiments, administered nanoceria particles of the invention are taken into cells through cell membranes and reside in the cellular cytoplasm or in various cellular organelles, such as the nucleus and mitochondria. In other embodiments, the nanoceria particles of the invention reside in intravascular or interstitial spaces, wherein they may reduce oxidative stress and inflammation by eliminating free radicals or reducing autoimmune responses. In a particular embodiment, the immune system invasion of the central nervous system resulting from breakdown of the blood-brain barrier (BBB) or blood-cerebrospinal fluid barrier (BCFB) or blood-ocular barrier (BOB) is modulated by nanoceria particles of the invention.

In another embodiment, the nanoceria particles of the invention are particles capable of crossing a mammalian blood brain barrier. In various embodiments, nanoceria particles of the invention cross a mammalian blood brain barrier and reside in brain parenchyma tissues as aggregates or agglomerates of a size less than about 100 nm, less than about 50 nm, less than about 20 nm, less than about 10 nm, less than about 5 nm. In a particular embodiment, nanoceria particles of the invention cross a mammalian blood brain barrier and reside in brain parenchyma tissues as independent, non-agglomerated nanoparticles of a size less than about 3.5 nm.

In particular embodiments, a pharmaceutical composition comprising nanoceria particles of the invention are specifically contemplated for prevention and/or treatment of oxidative stress related diseases and events, such as, but not limited to, Alzheimer's Disease, Parkinson's Disease, Huntington's Disease, amyotrophic lateral sclerosis (ALS), ataxia, Friedreich's ataxia, autism, obsessive-compulsive disorder, attention deficit hyperactivity disorder, migraine, stroke, traumatic brain injury, cancer, inflammation, autoimmune disorders, lupus, MS, inflammatory bowel disease, Crohn's Disease, ulcerative colitis, stenosis, restenosis, atherosclerosis, metabolic syndrome, endothelial dysfunction, vasospasms, diabetes, aging, chronic fatigue, coronary heart disease, cardiac fibrosis, myocardial infarction, hypertension, angina, Prizmetal's angina, ischemia, angioplasty, hypoxia, Keshan disease, glucose-6-phosphate dehydrogenase deficiency, favism, ischemic reperfusion injury, rheumatoid and osteo-arthritis, asthma, chronic obstructive pulmonary disease (e.g. emphysema and bronchitis), allergies, acute respiratory distress syndrome, chronic kidney disease, renal graft, nephritis, ionizing radiation damage, sunburn, dermatitis, melanoma, psoriasis, macular degeneration, retinal degeneration, cataractogenesis, among others.

In particular embodiments, a pharmaceutical composition comprising nanoceria particles of the invention are specifically contemplated for prevention and/or treatment of oxidative stress related cellular pathologies, such as, but not limited to, mitochondrial dysfunction, lysosome and proteasome dysfunction, oxidation of nucleic acids (e.g. RNA and DNA), tyrosine nitration, loss of phosphorylation mediated signaling cascades, initiation of apoptosis, lipid peroxidation and destruction of the membrane lipid environment.

In at least one embodiment, a pharmaceutical composition comprising cerium-containing nanoparticles made in accordance with the present invention are administered in an effective amount to prophylactically treat an oxidative stress related disease. As used herein, the phrase "effective amount" means an amount of a pharmaceutical composition comprising sufficient active principle (e.g. cerium-containing nanoparticles) to bring about the desired effect. The pharmaceutically effective amount, as recognized in the art, can be determined through routine experimentation.

In at least one embodiment, a pharmaceutical composition comprising cerium-containing nanoparticles made in accordance with the present invention are administered in an effective amount to treat symptoms of an oxidative stress related disease.

In various embodiments, a pharmaceutical composition comprising nanoceria particles of the invention is administered to a human or a non-human subject, such as another mammal, including, but not limited to, a canine, a feline, a bovine, an equine, an ovine, a porcine or a rodent. Alternatively, the subject of administration can be an animal such as a bird, insect, reptile, amphibian, or any companion or agricultural animal.

In various embodiments, nanoceria particles of the invention are administered in vivo to a subject by topical, enteral or parenteral methods, including injections, infusions or implantations. More particularly, it is specifically contemplated to administer nanoceria particles of the invention by any of the following routes: auricular (otic), buccal, conjunctival, cutaneous, dental, electro-osmosis, endocervical, endosinusial, endotracheal, enteral, epidural, extra-amniotic, extracorporeal, hemodialysis, infiltration, interstitial, intraabdominal, intra-amniotic, intra-arterial, intrabiliary, intrabronchial, intrabursal, intracardiac, intracartilaginous, intracaudal, intracavernous, intracavitary, intracerebral, intracisternal, intracorneal, intracornal-dental, intracoronary, intracorporus cavernosum, intradermal, intradiscal, intraductal, intraduodenal, intradural, intraepidermal, intraesophageal, intragastric, intragingival, intraileal, intralesional, intraluminal, intralymphatic, intramedullary, intrameningeal, intramuscular, intraocular, intraovarian, intrapericardial, intraperitoneal, intrapleural, intraprostatic, intrapulmonary, intrasinal, intraspinal, intrasynovial, intratendinous, intratesticular, intrathecal, intrathoracic, intratubular, intratumor, intratympanic, intrauterine, intravascular, intravenous, intravenous bolus, intravenous drip, intraventricular, intravesical, intravitreal, iontophoresis, irrigation, laryngeal, nasal, nasogastric, occlusive dressing technique, ophthalmic, oral, oropharyngeal, parenteral, percutaneous, periarticular, peridural, perineural, periodontal, rectal, respiratory (inhalation), retrobulbar, soft tissue, subarachnoid, subconjunctival, subcutaneous, sublingual, submucosal, topical, transdermal, transmammary, transmucosal, transplacenta, transtracheal, transtympanic, ureteral, urethral, vaginal, and any other or unassigned route.

In other embodiments, nanoceria particles of the invention are retained in or on the surface of a medical device or prosthesis, such as a cannula, catheter or stent, thereby reducing inflammation locally or systemically, over either a short or long time period.

In various embodiments, the nanoceria particles of the invention are delivered in any suitable form known in the art, including, but not limited to, a suspension, gel, tablet, enteric coated tablet, loaded liposome, powder, suppository, infusible, lozenge, cream, lotion, salve, or inhalant.

In various embodiments, the nanoceria particles of the invention are combined with other pharmaceutically acceptable substances, such as, but not limited to, water, salts, buffers, phosphate buffered saline (PBS), sugars, human or bovine serum albumen, lipids, drugs, colorants, flavorants, binders, gums, surfactants, fillers or any excipients known in the art.

In a particular embodiment, the vehicle comprising the nanoceria particles of the invention is sterilized prior to administration.

In other embodiments, a cell or cell culture is contacted with a nanoceria particle or particles of the invention. Contact may be practiced by exposing a cell or cell culture by in vitro or ex vivo methods, wherein the latter method comprises re-introducing the treated cell or cells into a subject, such as the subject from which the cell or cells were originally obtained. In various embodiments the cell is prokaryotic or eukaryotic in nature. In particular embodiments, the treated cells are used in the production of proteins used in the pharmaceutical industry, generally known as biologics, such as, but not limited to, antigens, antibodies and vaccines. In another embodiment, the treated cells are used in a fermentation process.

The invention is further illustrated by the following examples, which are not intended to limit the invention in any manner.

Experimental Section

Nanoparticle Light Scattering and Size Assessments

A simple qualitative characterization of the particle dispersions was performed by assessing the degree of Tyndell scattering exhibited by the dispersions when illuminated by a red laser pen light, relative to the amount of scattering from a sample of the neat solvent. A quantitative assessment of the particle size of the nanoparticle dispersions was performed by dynamic light scattering (DLS) using a Brookhaven 90Plus Particle Size Analyzer (Brookhaven Instruments Corp., Holtzville, N.Y., U.S.A.) equipped with a quartz cuvette. Reported DLS sizes are the lognormal number weighted parameter.

Nanoparticle Charge Assessment

A quantitative assessment of the nanoparticle charge was made by measuring the zeta potential using a Zetasizer Nano ZS from Malvern Instruments.

Preparation of Ceria Nanoparticles with Citric Acid and EDTA

Into a 800 ml glass beaker containing a magnetic stir bar was introduced 500 ml of high purity (HP) water. The water was then heated to about 70° C., and therein 2.41 gm of citric acid (CA) and 4.27 gm of ethylenediaminetetraacetic acid, disodium salt (EDTA) were dissolved. Ammonium hydroxide (28-30%) was added to adjust the pH of the solution to about 8.5. The temperature of the reaction vessel was raised to about 80° C., and the magnetic stir bar was replaced with a Silverson® L4RT high shear mixer operated at 5000 rpm. A 10.0 gm quantity of $Ce(NO_3)_3.6(H_2O)$ was dissolved in 30 ml of HP water, and this solution was added slowly to the stirred reaction mixture over several minutes. The reaction pH was maintained at about 8.5 by addition of small amounts of conc. $NH_4OH$ solution. Then a 50 ml solution containing 4.8 ml of 50% $H_2O_2$ (3.0 molar ratio of $H_2O_2$ to cerium) was added slowly over several minutes to the cerous ion, citric acid, EDTA reaction mixture. The reaction product was covered and then heated for an additional hour, resulting in a clear yellow/orange suspension. After cooling with stirring, the directly formed nanoparticle dispersion was washed by diafiltration to an ionic conductive of less than about 10 mS/cm, to remove excess salts. The pH of the product dispersion was about 7.2.

The final product dispersion was a clear yellow/orange liquid that displayed a high degree of Tyndall scattering when illuminated with a low intensity LASER beam, indicating it contained well-dispersed colloidal particles. The final product dispersion was observed to be stable for at least 12 months, with no indication of particle agglomeration or settling. Particle size analysis by dynamic light scattering on seven replicate preparations yielded an average hydrodynamic diameter of 3.1 nm with a standard deviation of 0.30 nm (COV of 10%).

Ceria nanoparticles prepared by this method wherein equimolar amounts (50/50) of citric acid and EDTA were added, are referred to herein variously as CA/EDTA ceria nanoparticles, CA/EDTA nanoceria, CeNPs, CNRx, or CNRx 87.

The replicate preparations of the CA/EDTA ceria nanoparticles were submitted for phase identification and crystallite size analysis by powder X-ray diffraction (XRD). Sample portions were placed in a Teflon boat, dried under a heat lamp for four hours, and then dried in an oven for four hours at 80° C. under vacuum. The resulting solids were lightly ground to form powders. These powders were then front-packed onto glass holders and analyzed by XRD in a N2 dry cell attachment.

Analysis of the XRD spectra of three particular replicate preparations of the CA/EDTA ceria nanoparticles shown in FIG. 1 indicated that each sample contained a major crystalline phase iso-structural with $CeO_2$ (PDF #34-394, cerianite). An average crystallite size of 2.4 nm with a standard deviation of 0.06 nm (COV of 2.5%) in the $CeO_2$ (220) direction was determined for the seven replicate samples using the Scherrer technique.

Figure 2:
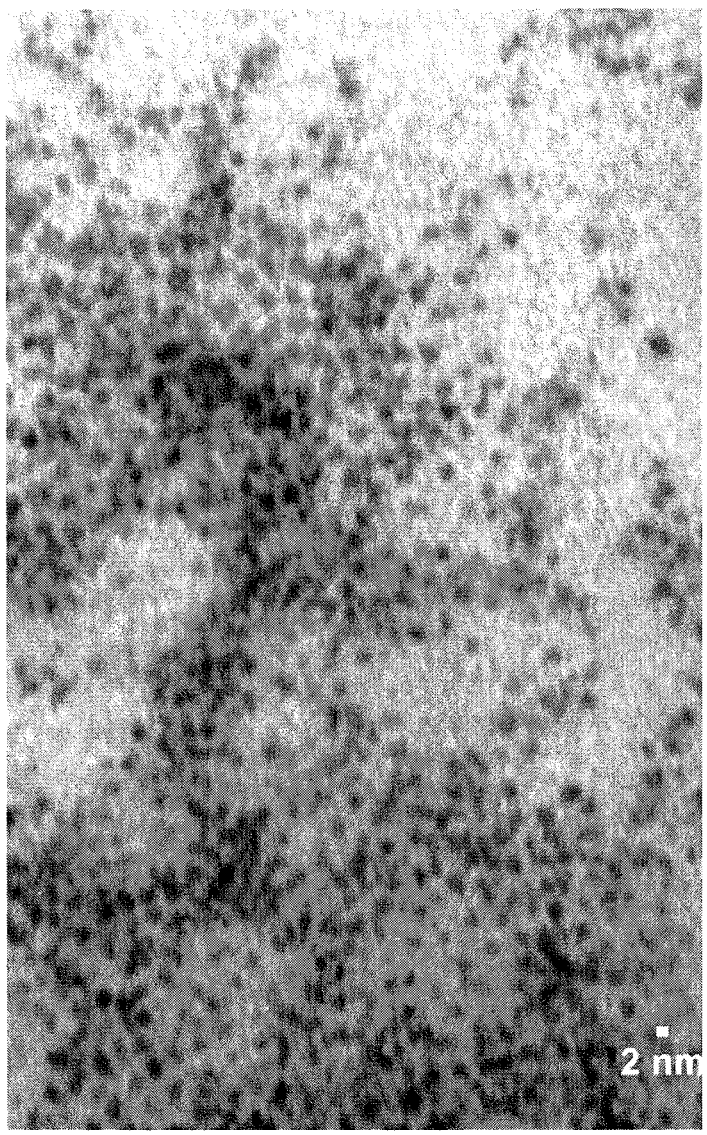
FIG. 2 is a TEM micrograph of dried down CA/EDTA ceria nanoparticles.

Moderately high resolution TEM micrographs of dried down CA/EDTA ceria nanoparticles (FIG. 2) revealed an ensemble of individual (non-agglomerated) particles with diameters on the order of 2-3 nm. Higher resolution TEM micrographs of dried down CA/EDTA ceria nanoparticles (FIG. 3) revealed individual arrays of atoms in selected nanoparticles. A size class distribution was determined from the TEM micrographs, as shown in FIG. 4.

Zeta potential measurements showed an average charge of ~23 mV for these aqueous dispersions of replicate preparations of CA/EDTA ceria nanoparticles.

The preparation of CA/EDTA ceria nanoparticles described above was repeated except that the molar ratio of citric acid and EDTA stabilizers was adjusted to 100/0, 80/20, 70/30, 60/40, 40/60, 30/70, 20/80 and 0/100, while maintaining a constant total molar amount of stabilizer. Stable dispersions of cerium oxide nanoparticles with substantially similar physical characteristics (particle size and zeta potential) resulted, as shown in Table 1 below.

Evaluation of Cerium Oxide Nanoparticles in Various Oxidative Stress Related Diseases Ischemic Stroke Mouse Hippocampal Brain Slice Model of Ischemic Stroke The ability of nanoceria to reduce oxidative stress was evaluated in a modification of the in vitro mouse hippocampal brain slice model of ischemia described by Estevez, A Y; et al., Neuroprotective mechanisms of cerium oxide nanoparticles in a mouse hippocampal brain slice model of ischemia, Free Radic. Biol. Med. (2011)51(6):1155-63 (doi: 10.1016/j.radbiomed.2011.06.006).

Adult (2-5 months of age) CD1 mice were sacrificed via rapid decapitation and their brains quickly removed and placed in a chilled choline-based slicing solution containing 24 mM choline bicarbonate, 135 mM choline chloride, 1 mM kynurenic acid, 0.5 mM $CaCl_2$, 1.4 mM $Na_2PO_4$, 10 mM glucose, 1 mM KCl, and 20 mM $MgCl_2$ (315 mOsm). Transverse hippocampal slices, 400 µm thick, were cut along a rostral-to-caudal axis (−1.2 to −2.8 mm Bregma) using a Leica VT1200 Vibratome (Leica Microsystems, Wetzlar, Germany) and allowed to recover for 1 hr in a control artificial cerebral spinal fluid (aCSF) containing 124 mM NaCl, 3 mM KCl, 2.4 mM $CaCl_2$, 1.3 mM $MgSO_4$, 1.24 mM $K_3PO_4$, 26 mM $NaHCO_3$, 10 mM glucose and bubbled with 5% $CO_2$, 95% $O_2$ gas (pH 7.4, 300 mOsm). Hippocampal slices were placed in a culture dish and stored in a NuAire humidified incubator (NuAire, Plymouth, Minn., USA) at 37° C. with 5% $CO_2$ for up to 48 hr.

Oxidative stress from ischemia was induced by placing the brain slices in hypoglycemic, acidic and hypoxic aCSF (glucose and pH were lowered to 2 mM and 6.8, respectively, and the solution was bubbled with 84% $N_2$, 15% $CO_2$, and 1% $O_2$) at 37° C. for 30 min. Sucrose was added to maintain the osmolarity of the solution at about 295 mOsm.

Aqueous dispersions of cerium oxide nanoparticles prepared as described supra were administered in matched dosage in a delivery volume of 1 µg per 1 ml aCSF or medium (equivalent to 5.8 µM) at the onset of the ischemic event, and remained in the medium throughout the remainder of the experiment. Control slices received an equal volume of vehicle control. Various delivery vehicles were used with similar success for the cerium oxide nanoparticles prepared as described herein, including distilled water alone, saline solution, Na-citrate solution, PBS, and combinations thereof.

After exposure to 30 minutes of oxidative stress (ischemic conditions), the living brain slices (test and control) were incubated for 24 hr in organotypic culture by placing them in a 35 mm culture dish containing culture medium and Millipore inserts (Millipore, Billerica, Mass., USA). Culture medium contained 50% minimum essential medium (Hyclone Scientific, Logan Utah, USA), 25% horse serum, 25% Hank's balanced salt solution (supplemented with 28 mM glucose, 20 mM HEPES and 4 mM $NaHCO_3$), 50 U/ml penicillin, and 50 µl/ml streptomycin, pH 7.2.

The extent of cell death was measured 24 hours after the oxidative injury using fluorescence imaging techniques. Each set of brain slices studied in the test condition (i.e. administered with cerium oxide nanoparticles) was matched with a similar set of control brain slices treated identically in every way except for administration of vehicle alone. Thus on each study day, two sets of anatomically matched brain slices taken from age-matched and sex-matched littermates were subjected to either the test condition (administered with cerium oxide nanoparticles) or control (vehicle alone). During fluorescence imaging measurements, the light intensity, duration of image capture, and timing of image collection were identical for the test condition and vehicle control brain slices. Results were expressed as the ratio of the fluorescence in the test condition to the fluorescence in the matched control slice imaged at the same time point in the experimental sequence.

At 24 hours post oxidative injury, paired (control and test) brain slices were incubated for 20 min in culture medium containing 0.81 µM vital exclusion dye SYTOX® Green (Invitrogen, Carlsbad, Calif., USA) and, subsequently, washed for 15-20 min in culture medium to remove unincorporated dye. SYTOX® Green is a fluorescent dye that binds to DNA and RNA. However, it is excluded from the cell nucleus by the cell membrane in intact, viable cells. Therefore, it acts as a vital dye and stains only those dead and dying cells in which the cell membrane has become permeable so that the dye has access to the cell interior. After staining and washing, brain slices were transferred to the stage of a Nikon TE 2000-U (Nikon Instruments, Melville, N.Y., USA) microscope equipped with epifluorescence attachments and a 150-W xenon light source (Optiquip, Highland Mills, N.Y., USA). Control aCSF solution was loaded into 60-ml syringes, equilibrated with 95% $O_2$/5% $CO_2$, and heated to 37° C. using a servo-controlled syringe heater block, stage heater, and in-line perfusion heater (Warner Instruments, Hamden, Conn., USA). The brain sections were continuously perfused with warmed, 95% $O_2$/5% $CO_2$ equilibrated aCSF at a rate of 1 ml per minute. After 5 min, images of the hippocampal formation of each control and test brain slice were collected using a 4× Plan Flour objective (Nikon Instruments) under identical conditions (i.e. light intensity, exposure time, camera acquisition parameters). SYTOX® Green fluorescence was measured by briefly (620 ms) exciting the tissue at 480±40 nm, filtering the emitted fluorescence (535±50 nm) from the probe using a 505 nm, long-pass, dichroic mirror (Chroma technology, Bennington, Vt., USA), intensifying, and measuring with a cooled CCD gain EM camera (Hamamatsu CCD EM C9100; Bridgewater, N.J., USA). The digital images were acquired and processed with Compix SimplePCI 6.5 software (C Imaging Systems, Cranberry Township, Pa., USA).

The light intensity resulting from the SYTOX® Green loading reflected the number of dead or dying cells within the calculated area. The light-intensity measurements were performed automatically using the Compix SimplePCI 6.5 software, thereby eliminating experimenter bias in selecting the regions of interest.

Reduction in cell death is reported as the ratio of the light intensity of SYTOX® Green fluorescence from the cornu ammonis fields (oriens layer, stratum radiatum and lacunosum moleculare) for the test condition (i.e. nanoceria treated) to the control (untreated) for anatomically matched hippocampal sections taken from age-matched and sex-matched littermate brains sliced and exposed to ischemic oxidative stress on the same day, and fluorescence imaged 24 hr after the ischemic insult.

Cerium oxide nanoparticles prepared with biocompatible stabilizers comprising citric acid, EDTA and combinations thereof, were evaluated in the Mouse Hippocampal Brain Slice Model of Ischemic Stroke using a treatment concentration of 5.8 µM. Results for the reduction in cell death (percent reduction relative to control), commonly referred to as sparing, as a function of citric acid to EDTA molar ratio are given in Table 1 below.

TABLE 1

| CA/EDTA Ratio | Particle Size | | Sparing Results | | Sparing Synergy | |
|---|---|---|---|---|---|---|
| | XRD (nm) | DLS (nm) | Actual (%) | Predictive (%) | Actual - Predictive (%) | Actual/ Predictive |
| 100/0 | 2.0 | 7.8 | 15.5 | 15.5 | 0 | 1 |
| 80/20 | 2.4 | 3.4 | 6.0 | 12.8 | −6.8 | 0.5 |
| 70/30 | 2.3 | 3.8 | 21.6 | 11.4 | 10.2 | 1.9 |
| 60/40 | 2.4 | 2.6 | 11.3 | 10.0 | 1.3 | 1.1 |
| 50/50 | 2.4 | 3.1 | 30.3 | 8.65 | 21.65 | 3.5 |
| 40/60 | 2.5 | 2.9 | 26.3 | 7.3 | 19.0 | 3.6 |
| 30/70 | 2.5 | 3.0 | 23.0 | 5.9 | 17.1 | 3.9 |
| 20/80 | 2.4 | 3.5 | 6.9 | 4.5 | 2.4 | 1.5 |
| 0/100 | 2.1 | 2.4 | 1.8 | 1.8 | 0 | 1 |

Treatment with cerium oxide nanoparticles prepared with citric acid alone as a stabilizer (100/0) reduced cell death (sparing) by about 16%, whereas treatment with cerium oxide nanoparticles prepared with EDTA alone as a stabilizer (0/100) had little effect on cell death (1.8% reduction). Further reduction in cell death, alternative termed an increase in sparing, is a desirable feature of a pharmaceutical composition or medicament. Treatment with cerium oxide nanoparticles prepared with a combination of citric acid and EDTA in a molar ratio ranging from 70/30 to 20/80 resulted in surprising increases in sparing that substantially exceeded the simple linear predictive additive sum based on the effects of each stabilizer used alone. For example, the greatest sparing (about 30%) was seen for the equimolar (50/50) ratio of citric acid to EDTA, whereas the simple linear prediction for nanoparticles prepared with this combination of stabilizers is the average of a 15.5% sparing for citric acid alone and a 1.8% sparing for EDTA alone, which is only an 8.65% sparing. Thus a surprising and unexpected synergy between the combination of citric acid and EDTA stabilizers has been discovered, wherein the actual sparing for equimolar (50/50) citric acid and EDTA is about 3.5 times larger than the simple linear prediction.

In general, a simple linear (additive) model for the Predictive sparing percent for a given ratio of citric acid to EDTA, is given by the expression:

[Fraction of CA]*[Sparing % of CA]+[Fraction of EDTA]*[Sparing % of EDTA]

wherein the fraction of a given stabilizer is the molar fraction of the total stabilizer present. For the results shown in Table 1, Sparing % of CA is 15.5%, and Sparing % of EDTA is 1.8%. The values of this expression (Predictive sparing percent) are tabulated above in Table 1 in the column headed by Sparing Results and Predictive (%).

In general, the synergistic increase in sparing can be embodied in two distinct parameters. The difference between the Actual and Predictive sparing amounts (Actual−Predictive) embodies the synergy on an absolute basis, for which a positive value represents unexpected additional sparing (inventive result), and a negative value represent less than the expected amount of sparing (i.e. a negative interaction or interference between the stabilizers). Alternatively, the ratio of Actual to Predictive (Actual/Predictive) embodies the synergy on a relative basis, for which a value greater than one represents the relative amount of additional unexpected sparing (inventive result), and a value less than one represents the relative amount of sparing less than the Predictive expected amount due to a negative interaction or interference between the stabilizers (comparative result).

Examination of these parameters in the Sparing Synergy columns in Table 1 reveals, once more, that treatment with cerium oxide nanoparticles prepared with a combination of citric acid and EDTA in a molar ratio ranging from 70/30 to 20/80 resulted in a synergistic increase in absolute sparing (the value of (Actual−Predictive) is positive) along with a synergistic increase in relative sparing (the value of (Actual/Predictive) is greater than one). The greatest amount of absolute synergistic sparing increase occurs for the treatment ratio of citric acid to EDTA of 50/50, for which an additional 21.65% of sparing is unexpectedly observed. The greatest amount of relative synergist sparing increase occurs for the treatment ratio of citric acid to EDTA of 30/70, for which the Actual sparing is 3.9 times greater than the Predictive.

In contrast, a negative interaction or interference is observed for the treatment with cerium oxide nanoparticles prepared with a combination of citric acid and EDTA in a molar ratio of 80/20, for which the absolute Actual sparing was 6.8% less than the Predictive, or, alternatively, the relative Actual sparing was only one-half (0.5 times) that of the Predictive.

Thus, in summary, it has been discovered that treatment with cerium oxide nanoparticles prepared with molar ratios of citric acid to EDTA in a range of about 3.0 to about 0.1 resulted in a synergistic increase in sparing, whereas treatment with cerium oxide nanoparticles prepared with a molar ratio of citric acid to EDTA of 4.0 resulted in an interference leading to less than the expected sparing.

Multiple Sclerosis

Multiple sclerosis (MS) is a disease of the central nervous system (CNS) that affects more than 2 million people worldwide. MS has long been considered an immune mediated inflammatory disease leading, in part, to the degeneration of the myelin sheath surrounding nerve cells and, ultimately, neuronal cell death due to oxidative stress. The most common course of the disease, termed relapse/remitting, is characterized by clearly defined attacks of worsening neurological and motor function, followed by periods of relative quiet (remission) with no new signs of disease activity. A less common course of the disease is termed chronic-progressive MS and is characterized by a steady progression of clinical neurological damage, without remission after initial MS symptoms. While only about 20% of patients are initially diagnosed with chronic-progressive MS, about half of those initially diagnosed with relapse/remitting MS will progress to the chronic-progressing form with the passage of each decade.

Chronic-Progressive Multiple Sclerosis

Murine EAE Model of MS

Many of the pathological features of the onset of MS are modeled by the murine experimental autoimmune encephalomyelitis (EAE) model, wherein an inflammatory disorder is induced by immunization with myelin antigens. The EAE model is characterized by blood-brain-barrier (BBB) breakdown, perivascular infiltration of immune cells, microglia activation, and demyelination. The EAE model has been critical in the development of current therapies used in the treatment of MS.

SJL-EAE mice were purchased from Jackson Laboratories (C57BL/6) and treated with vehicle or vehicle plus CA/EDTA ceria nanoparticles. The CA/EDTA ceria nanoparticles mixed in PBS/50 mM sodium citrate saline were administered to experimental animals by IV tail vein injection either before (preventative model) or after (therapeutic model) disease induction and then were given maintenance doses of different concentrations.

In one experiment a subset of mice were treated daily with the immunomodulatory drug fingolimod (Cayman Chemical, Ann Arbor, Mich., USA) at 2 µg/L in the drinking water. The various treatment regimens (dosing regimens) are described in detail in Table 4 below.

TABLE 4

| Administration Regimen* | Day before induction | Induction day | Day 3 post-induction | Maintenance doses: Day 7 and weekly thereafter |
|---|---|---|---|---|
| Preventative | 15 mg/kg CeNPs | 15 mg/kg CeNPs | 10, 20, or 30 mg/kg CeNPs | 10, 20, or 30 mg/kg CeNPs |
| Therapeutic: 3 Day Delay | — | — | 10, 20, or 30 mg/kg CeNPs | 10, 20, or 30 mg/kg CeNPs |
| Therapeutic: 7 Day Delay | — | — | — | 30 mg/kg CeNPs or Fingolimod** |

The mice were induced with experimental autoimmune encephalomyelitis (EAE), i.e. chronic-progressive multiple sclerosis-like symptoms, as follows: a 0.1 ml intravenous (IV) tail injection of 200 µg myelin oligodendrocyte ($MOG_{35-55}$) protein peptide (Genscript) dissolved in phosphate buffered saline (PBS) mixed with an equal volume of complete Freund's adjuvant, was followed by an 0.1 ml intraperitoneal injection of 200 ng pertussis toxin in PBS was delivered on Days 0 and 2.

Disease progression was scored daily using a Clinical Scoring Test described below, along with the three Motor Behavior Tests designed to evaluate cerebellar function (Balance Beam), forelimb strength (Hanging Wire), and hindlimb strength (Rotarod).

Clinical Scoring Test

Disease progression of multiple sclerosis type symptoms in the EAE mice was scored daily using a clinical scale adapted from Selvaraj et al. (2008), as shown in the Table 2 below.

TABLE 2

| Disease Score | Symptoms |
|---|---|
| 0 | Normal movement; no paralysis |
| 0.5 | Limp tail, tail drags when the mouse walks. Mouse can, however, curl tail when lifted |
| 1.0 | Full tail paralysis; tail drags when the mouse walks. Mouse cannot curl tail when lifted |
| 2.0 | Partial limb paralysis; limp tail; mouse walks with a clumsy (wobbly) gait; no complete paralysis of any limbs |
| 2.5 | Partial limb paralysis; limp tail; mouse cannot walk, limbs can still move when mouse is lifted |
| 3.0 | One hind limb fully paralyzed; limp tail; mouse drags hind legs, but can still move around |
| 3.5 | Both hind limbs fully paralyzed; limp tail, mouse drags hind legs, but can still move around and eat |
| 4.0 | Both hind limbs paralyzed, one front limb paralyzed; limp tail, movement severely impaired; mouse sacrificed |

Motor Behavior Tests

Hanging Wire Test

A hanging wire task was used to assess grip strength. For this task, mice were placed in an open-top Plexiglas box with a steel wire grid floor. The box was turned upside down 60 cm above the counter top, and latency to fall was measured.

Rotarod Test

A rotarod apparatus (Med Associates, St. Albans, Vt.) was used to assess mainly hind limb motor coordination and endurance. Mice were placed onto a drum rotating at 28 rpm and latency to fall from the drum (300 seconds, maximum) was measured.

Balance Beam Test

For this task, mice were placed on the illuminated end of an elevated wooden beam and given up to 60 s to reach the goal box. Balance and gait quality were scored using a 5 point scale (5=normal gait to 0=falls off beam immediately). Gait quality was further rated according to the scale described below.

TABLE 3

| 0 | Falls off beam |
|---|---|
| 1 | Clings to beam; DOES NOT move with prodding |
| 2 | Clings to beam for max time; DOES move with prodding: SCOOCHES |
| 2.5 | Clings to beam for max time; DOES move with prodding: WALKS |
| 3 | Alternates clinging and moving: SCOOCHES; DOES NOT walk entire beam in allowed time |
| 3.5 | Alternates clinging and moving: WALKS; DOES NOT walk entire beam in allowed time |
| 4 | Paces beam but DOES NOT reach goal box in allowed time OR alternates clinging and moving: WALKS; DOES walk entire beam in allowed time |
| 5 | Traverses entire beam without difficulty within time allowed |

Figure 5:
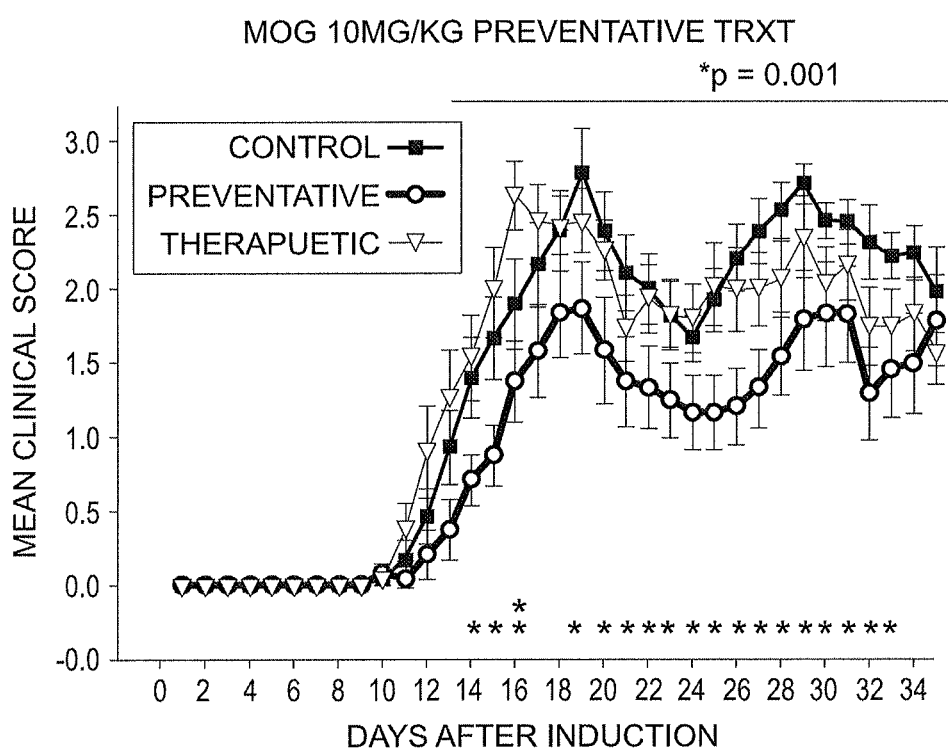
FIG. 5 is a plot of Mean Clinical Score as a function of time for the chronic-progressive model of MS for vehicle control and for CeNPs administered in the preventative and therapeutic treatment regimens. Drug (CeNPs) treatment dosage was 10 mg/kg.
Figure 6:
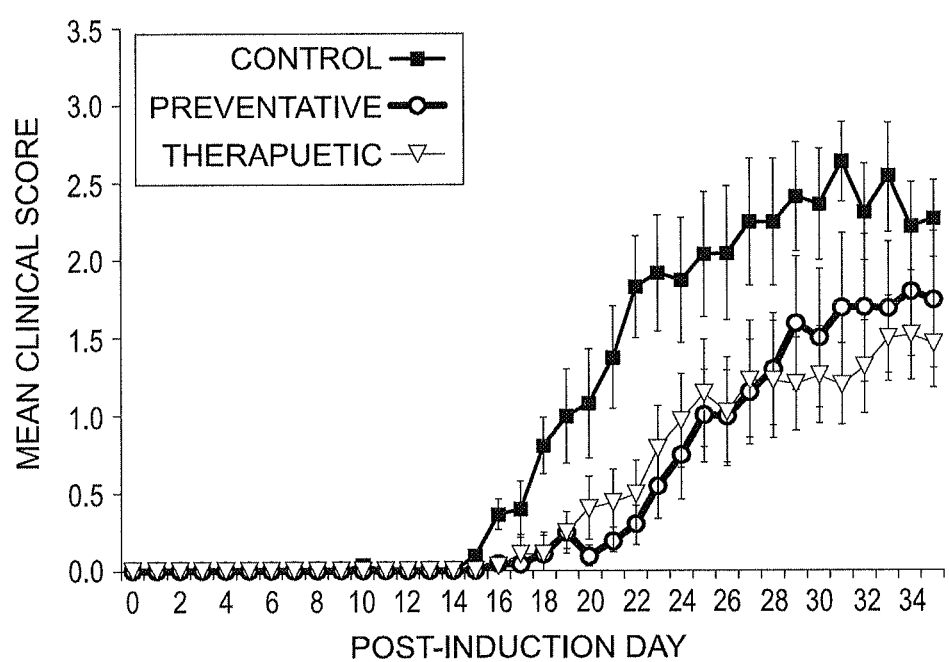
FIG. 6 is a plot of the Mean Clinical Score as a function of time in the chronic-progressive model of MS for the vehicle control, preventative and therapeutic treatment regimen. Drug (CeNPs) treatment dosage was 20 mg/kg.
Figure 7:
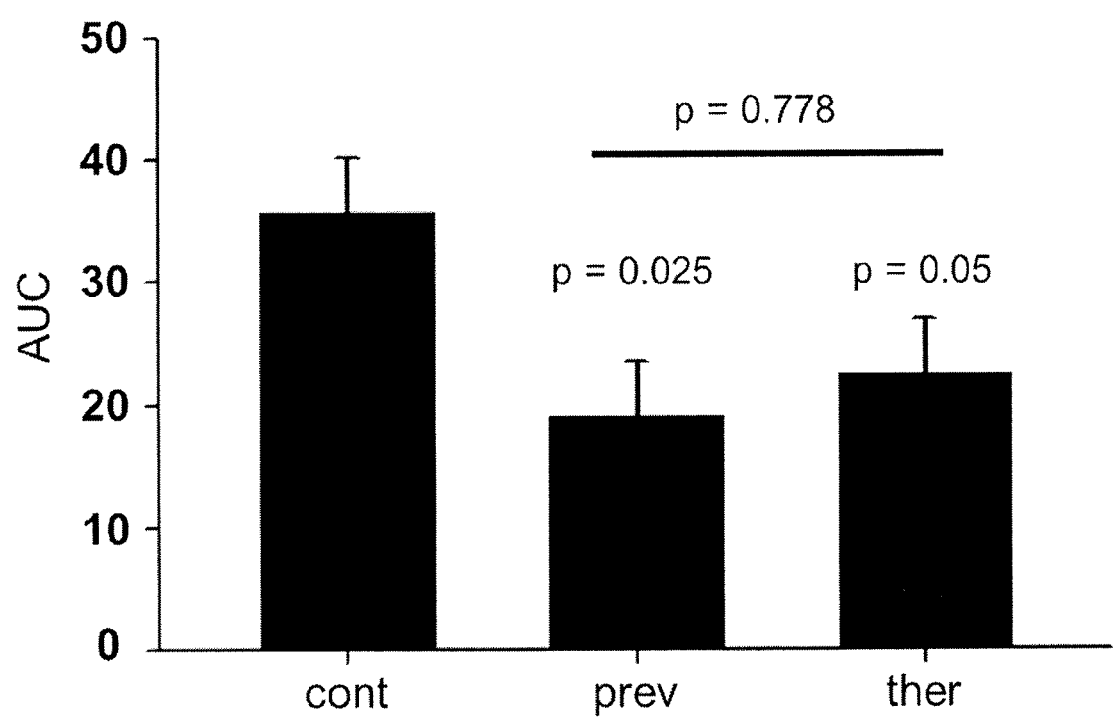
FIG. 7 is a chart Clinical Score (AUC) over the disease course for the chronic-progressive model of MS for the vehicle control (cont) and for CeNPs administered by the preventative (prev) and the therapeutic (ther) treatment regimens. Drug (CeNPs) treatment dosage was 20 mg/kg.
Figure 8:
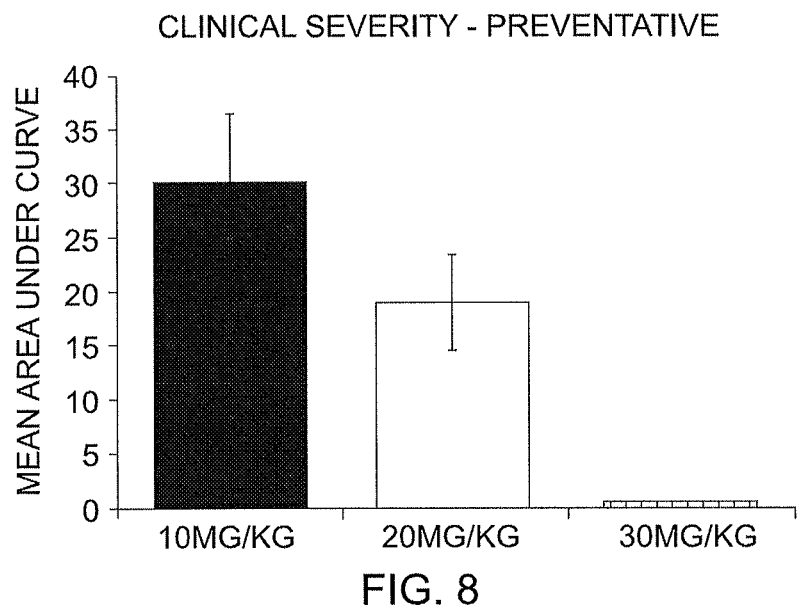
FIG. 8 is a chart of the Clinical Severity (AUC) of the chronic-progressive model of MS as a function of CeNPs dosage for the preventative treatment regimen.
Figure 9:
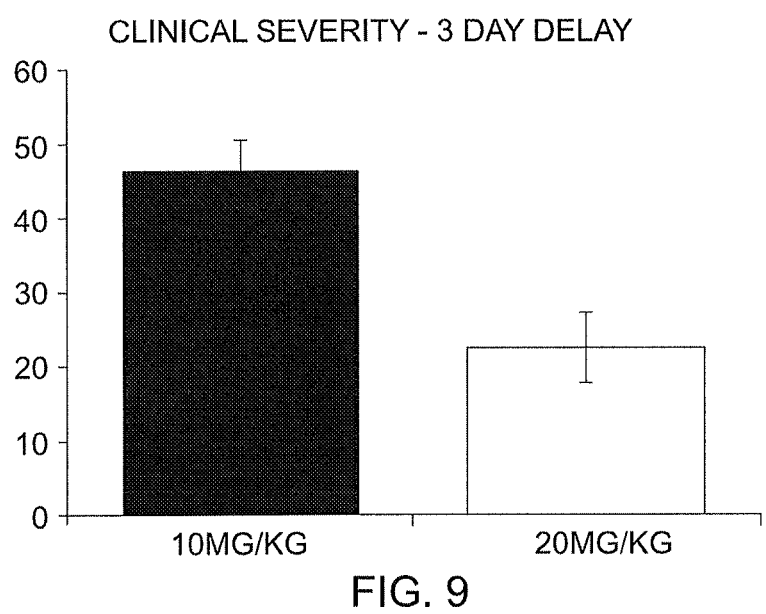
FIG. 9 is a chart of the Clinical Severity (AUC) of the chronic-progressive model of MS as a function of CeNPs dosage for the therapeutic (3 Day Delay) treatment regimen.

CA/EDTA ceria nanoparticles decreased (improved) Clinical Scoring results for both the Preventative and Therapeutic dosing designs are shown for the 10 mg/kg dosage in FIG. 5, and for the 20 mg/kg dosage in FIG. 6. As a measure of cumulative disease severity, the area under the curve (AUC) of Mean Clinical Score vs. Post-Induction Day (see FIG. 7), was calculated for each animal dosed at the 20 mg/kg level. CA/EDTA ceria nanoparticles decreased (improved) Clinical Severity in a dose-dependent manner for the Preventative treatment regime (FIG. 8) and the Therapeutic 3 Day Delay treatment regime (FIG. 9). An overall view of the reduction in disease severity as a function of total ceria injected is shown in FIG. 10.

Tissue accumulation of ceria: a subset of mice was euthanized by isoflurane overdose and transcardially perfused with PBS. Harvested tissues were frozen and analyzed for cerium by inductively coupled plasma mass spectrometry (ICP-MS). Brain cerium content as a function of total ceria injected is shown in FIG. 11.

Figure 10:
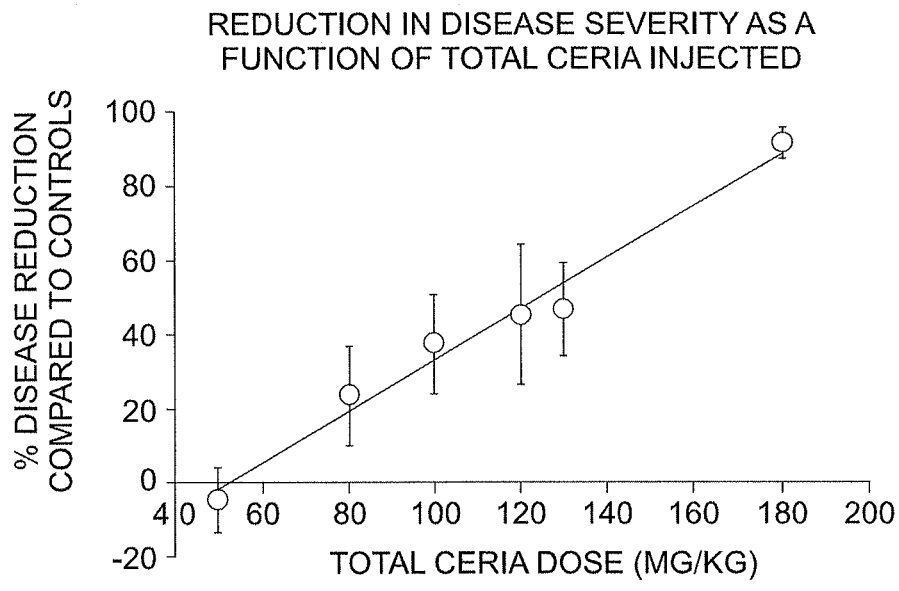
FIG. 10 is a plot of Reduction in Disease Severity as a function of total ceria (CeNPs) injected into the chronic-progressive model of MS.
Figure 11:
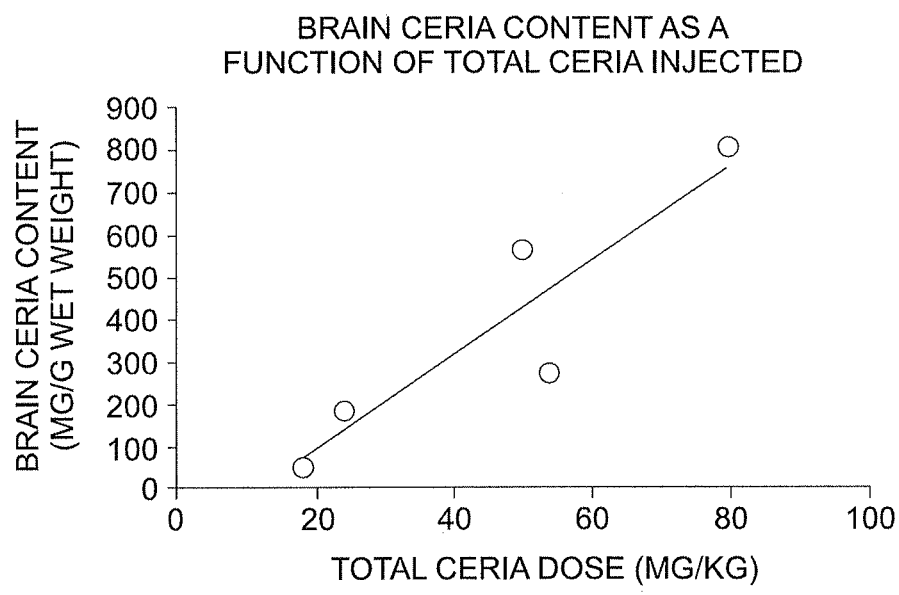
FIG. 11 is a plot of Brain Cerium Content as a function of total ceria (CeNPs) injected into the chronic-progressive model of MS.
Figure 12:
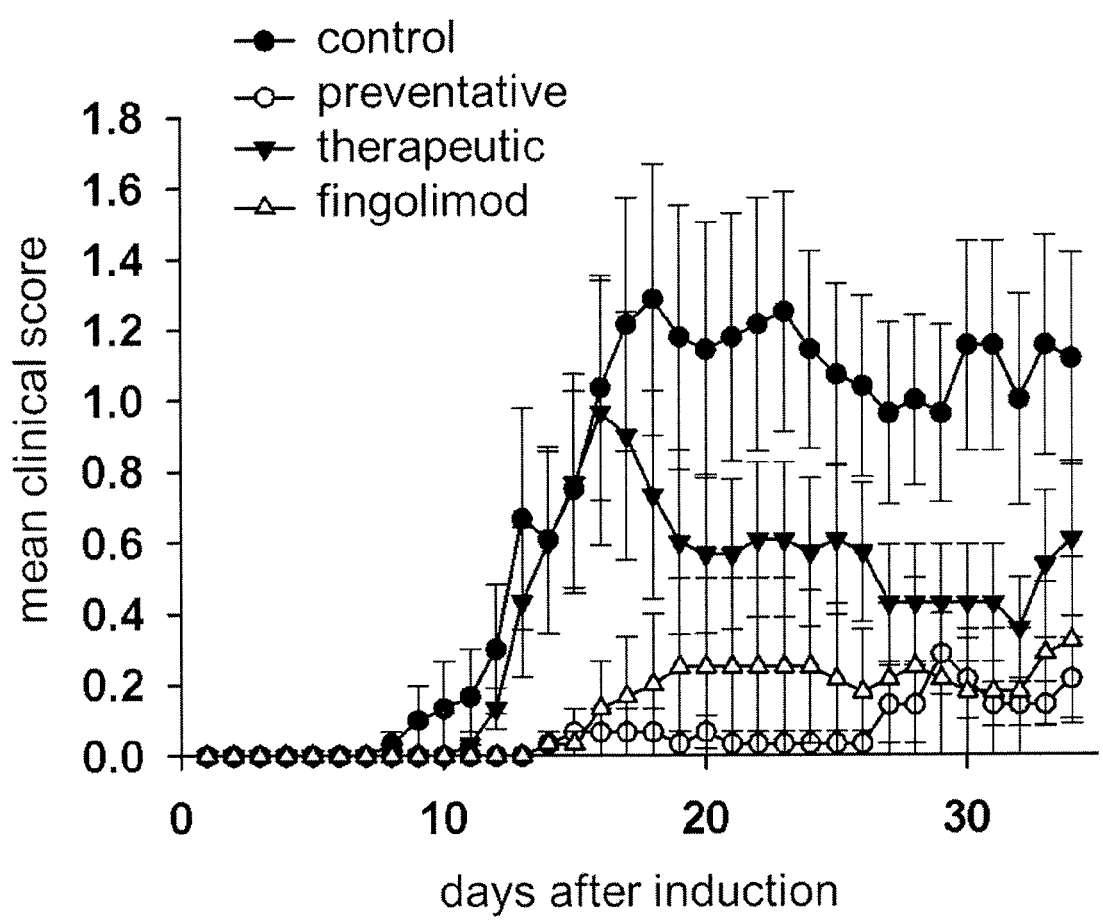
FIG. 12 is a plot of Mean Clinical Score as a function of time for the chronic-progressive model of MS for the control, for CeNPs administered in the preventative and therapeutic treatment regimens, and for daily fingolimod treatments. Drug (CeNPs) treatment dosage was 30 mg/kg.
Figure 13:
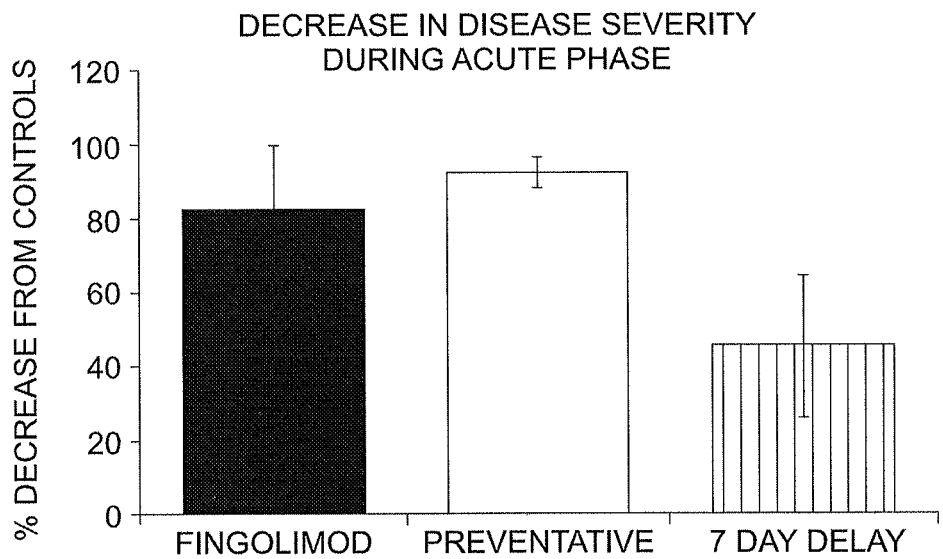
FIG. 13 is a chart of Decrease in disease severity during the acute phase (days 0-30) of the chronic-progressive model of MS, relative to controls, for Fingolimod, and for CeNPs administered by the preventative and therapeutic (7 Day Delay) treatment regimens.

The results of FIGS. 10-11 suggest that particle penetrance into the CNS correlates well with dose delivered and is not saturated at the range of doses tested.

Figure 14:
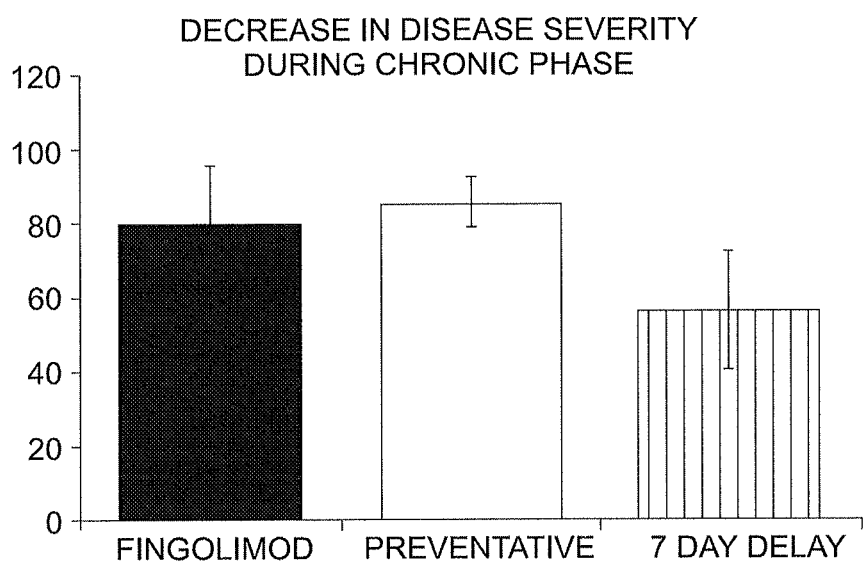
FIG. 14 is a chart of Decrease in Disease Severity during the chronic phase (days 31-35) of the chronic-progressive model of MS, relative to controls, for Fingolimod and for CeNPs administered by the preventative and therapeutic (7 Day Delay) treatment regimens.
Figure 15:
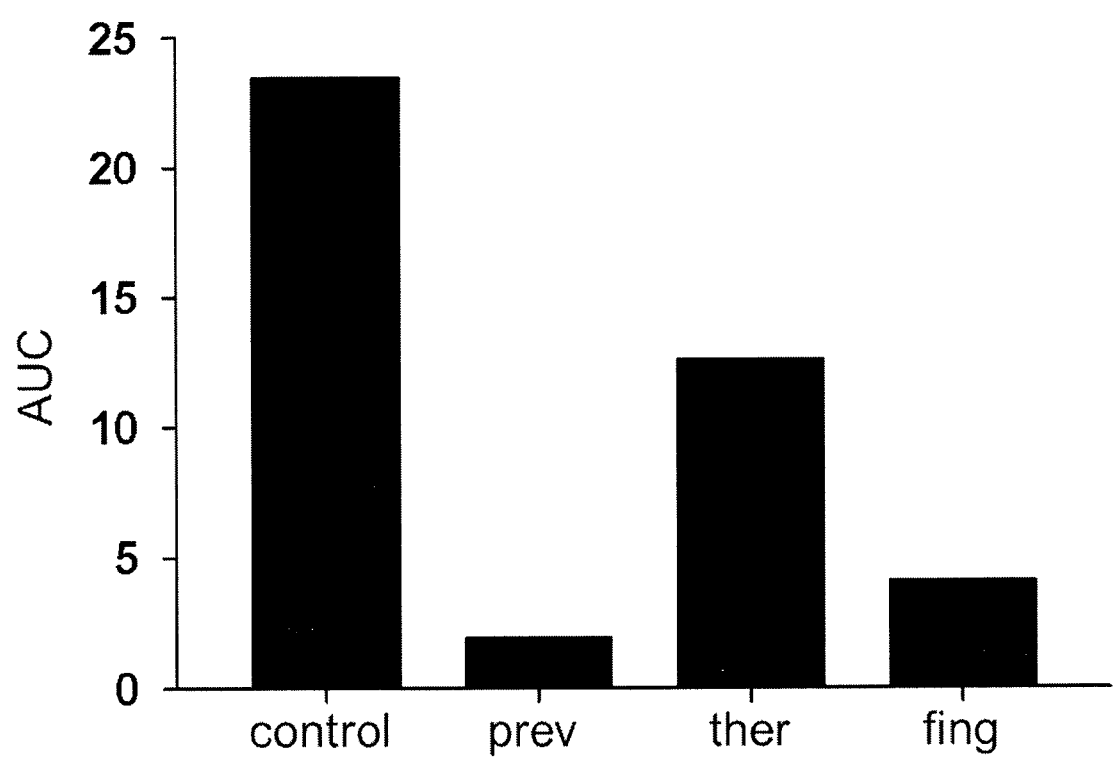
FIG. 15 is a chart assessing disease severity (AUC) through the entire disease course for the chronic-progressive model of MS for the Control, for CeNPs administered by the preventative (prev) and therapeutic (7 Day Delay) (ther) regimens, and for the Fingolimod (fing) daily treatment regimen.

Comparison of CA/EDTA ceria nanoparticles dosed at the 30 mg/kg level to the immunomodulatory drug Fingolimod is shown in results of FIGS. 12-15. All treatment groups significantly reduced disease severity relative to controls during both the A) acute (FIG. 13) and B) chronic phases (days 31-35) of the disease (p<0.05) (FIG. 14). The Fingolimod and Preventative treatments were significantly more effective that the Therapeutic (7 Day Delay) treatment during the acute phase. All groups were equally effective during the chronic phase of the disease (Days 31-35).

Figure 16:
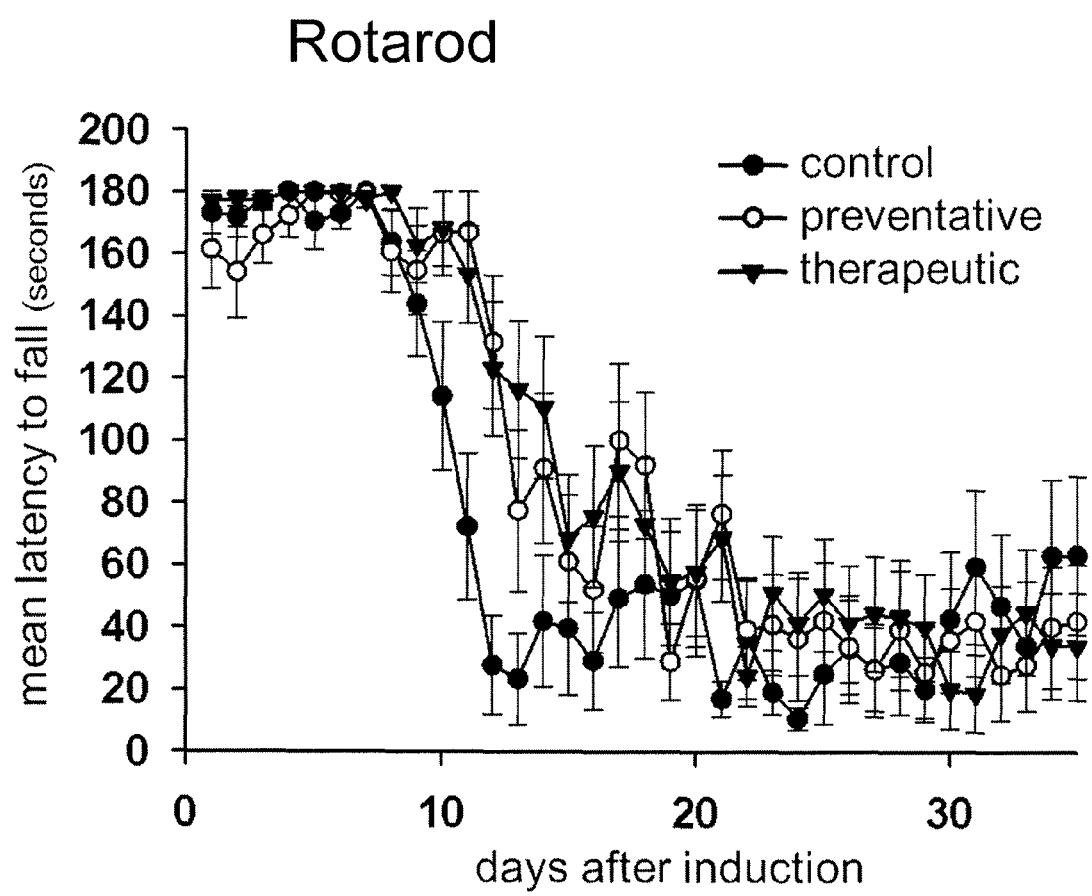
FIG. 16 is a plot of Rotarod Test performance as a function of time for the chronic-progressive model of MS for the control and for CeNPs administered by the preventative and therapeutic treatment regimens. Drug (CeNPs) treatment dosage was 20 mg/kg.
Figure 17:
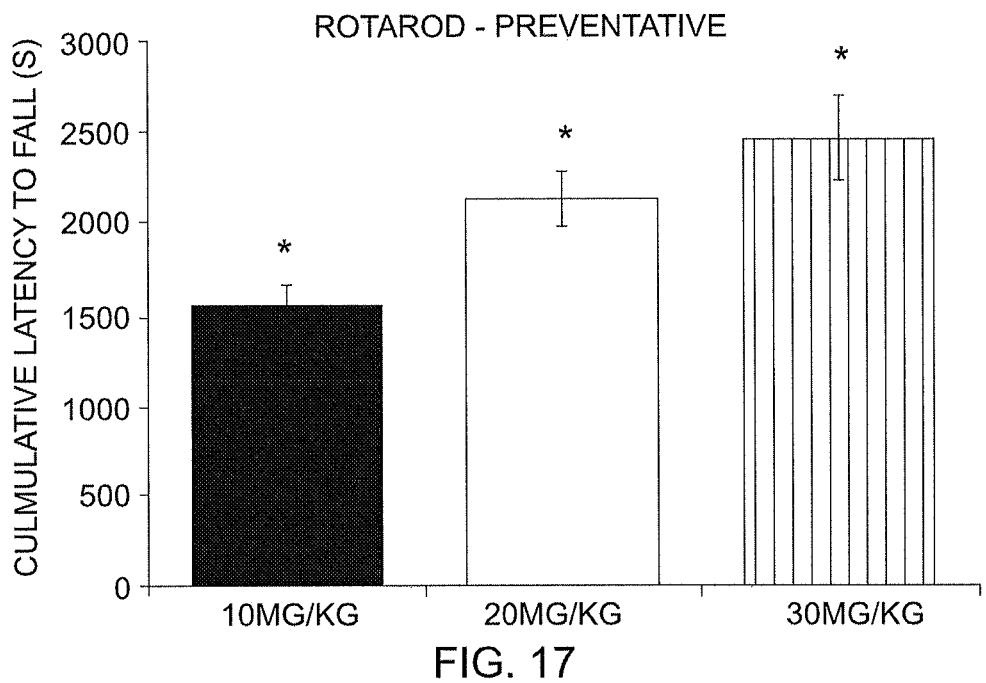
FIG. 17 is a chart of Rotarod Test performance for the chronic-progressive model of MS as a function of CeNPs dosage administered by the preventative treatment regimen.
Figure 18:
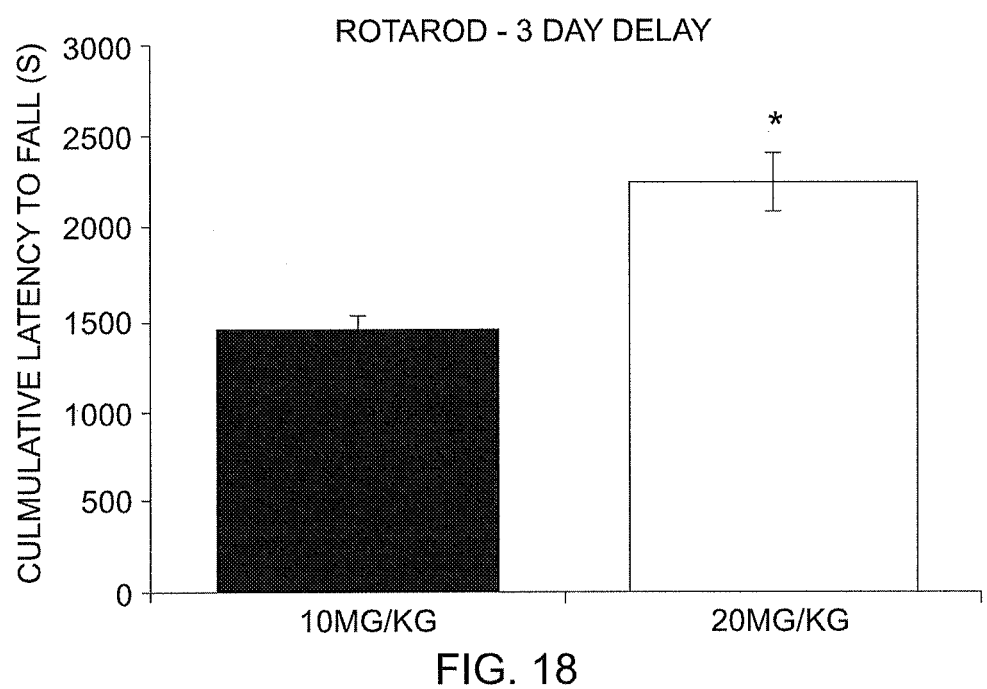
FIG. 18 is a chart of Rotarod Test performance for the chronic-progressive model of MS as a function of CeNPs dosage administered by the therapeutic (3 Day Delay) treatment regimen.
Figure 19:
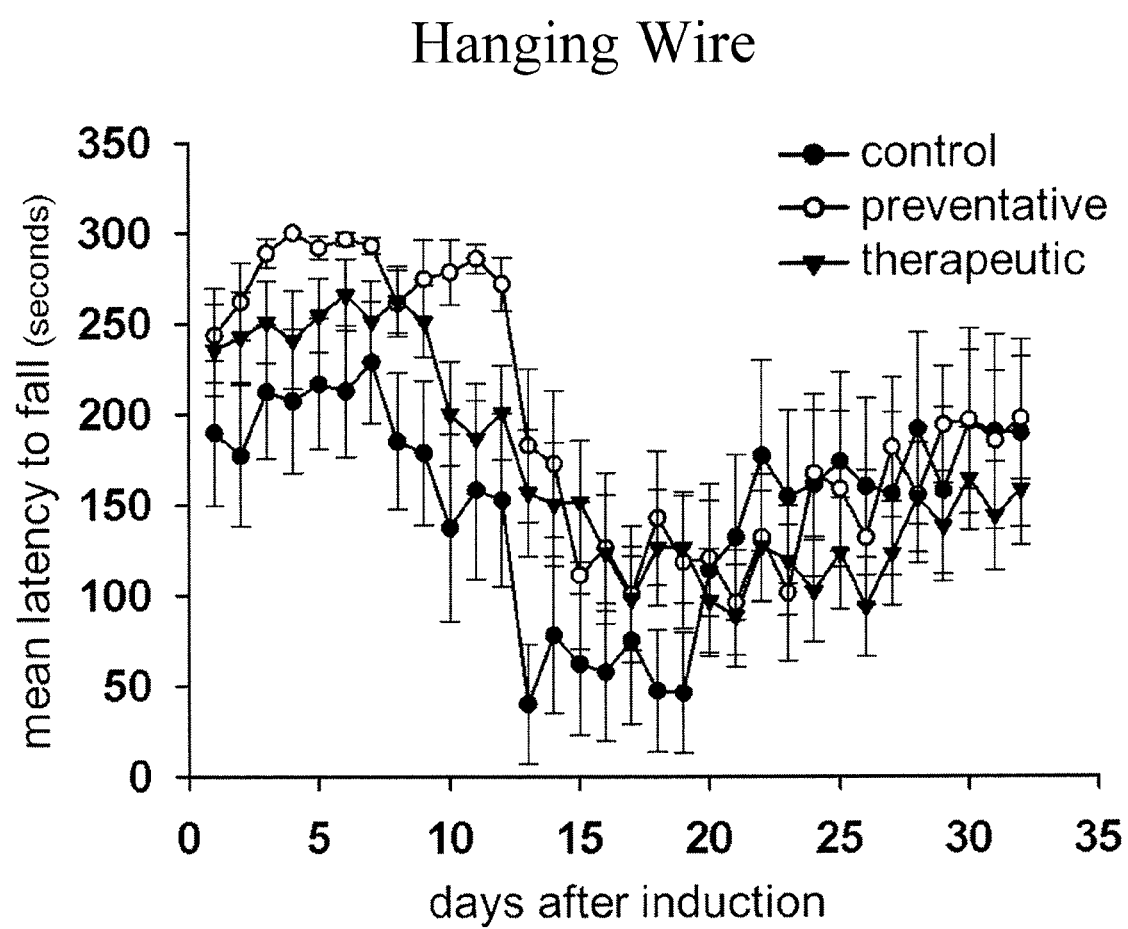
FIG. 19 is a plot of Hanging Wire Test performance as a function of time for the chronic-progressive model of MS for the control and for CeNPs administered by the preventative and therapeutic treatment regimens. Drug (CeNPs) treatment dosage was 20 mg/kg.
Figure 20:
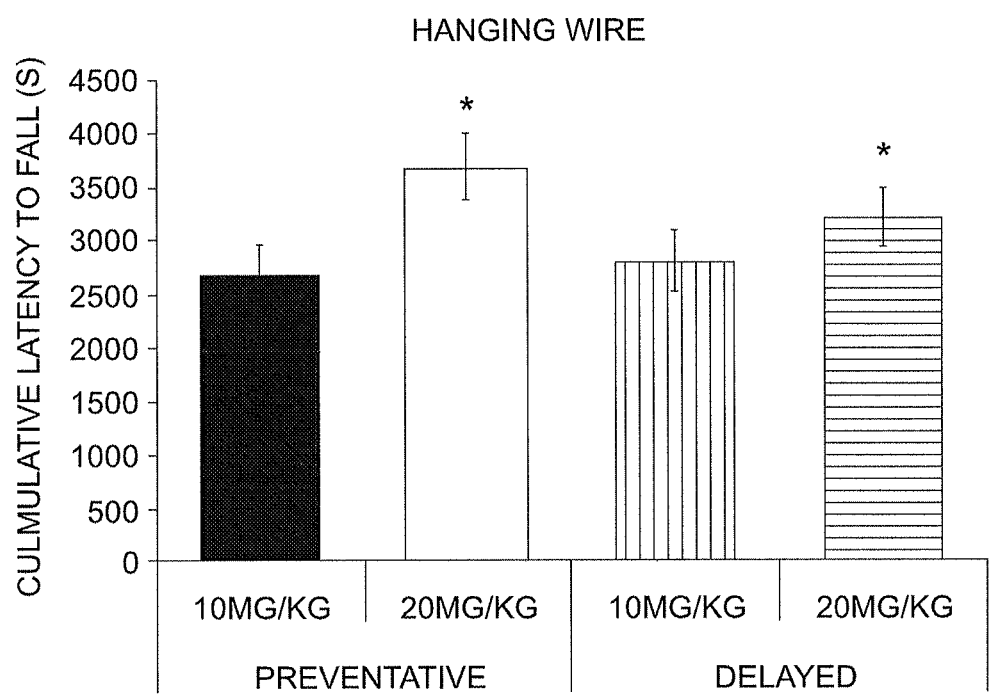
FIG. 20 is a chart of Hanging Wire performance for the chronic-progressive model of MS as a function of CeNPs dosage administered by the preventative and therapeutic (Delayed) treatment regimens.
Figure 21:
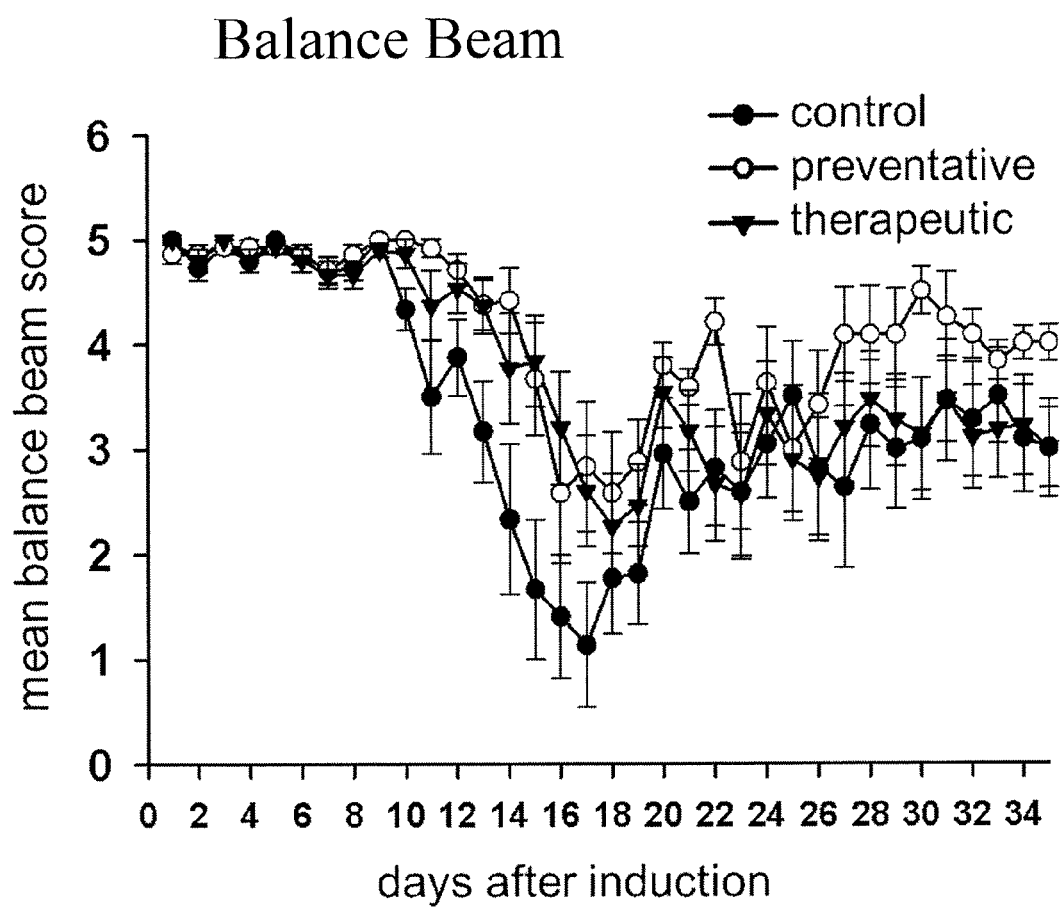
FIG. 21 is a plot of Balance Beam Test performance as a function of time for the chronic-progressive model of MS for the control and for CeNPs administered by the preventative and therapeutic treatment regimens. Drug (CeNPs) treatment dosage was 20 mg/kg.
Figure 22:
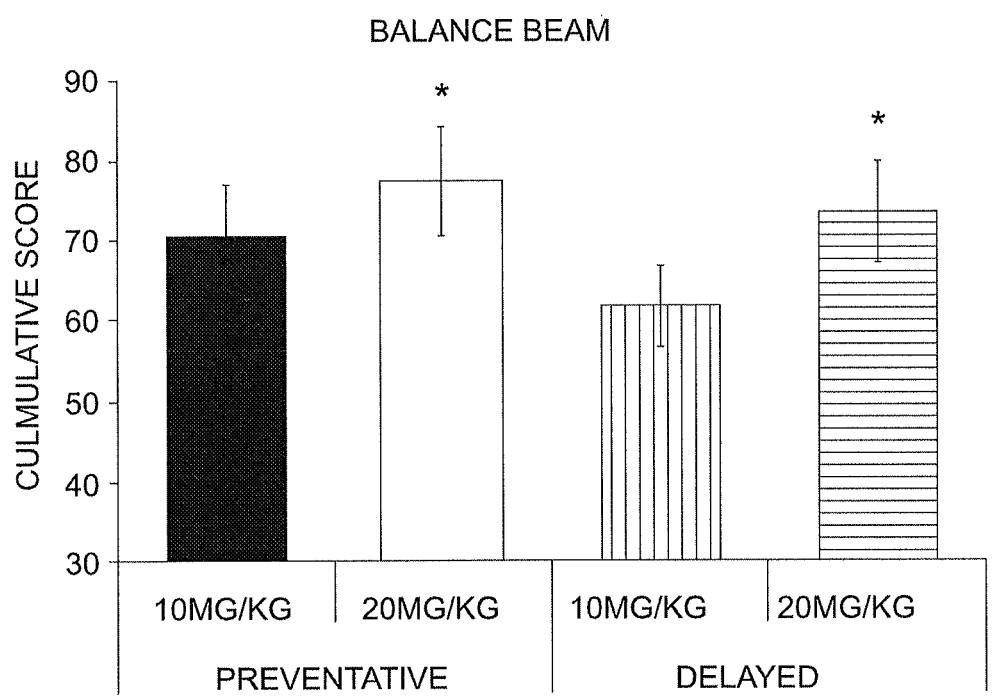
FIG. 22 is a chart of Balance Beam Test performance for the chronic-progressive model of MS as a function of CeNPs dosage administered by the preventative and therapeutic (Delayed) treatment regimens.

In addition, treatment with the CA/EDTA ceria nanoparticles improved the motor behavior performance of the mice. Daily group average motor behavior performance for mice receiving the 20 mg/kg dosage of the CA/EDTA ceria nanoparticles is shown for the Rotorod test (FIG. 16) and Hanging Wire Test (FIG. 19), wherein a longer latent time to fall relative to the control indicates improved motor performance. Daily group average Balance Beam performance for the 20 mg/kg dosage is shown in FIG. 21, wherein a higher score relative to the control indicates improved motor performance. Motor behavior performance continued to improve with increasing dosage over the ranges studied, as shown for the Rotarod Test for both the Preventative (FIG. 17) and Therapeutic 3 Day Delay (FIG. 18) treatment regimes, and for the Hanging Wire Test (FIG. 20) and the Balance Beam Test (FIG. 22) for all doses and treatment regimes.

Figure 23:
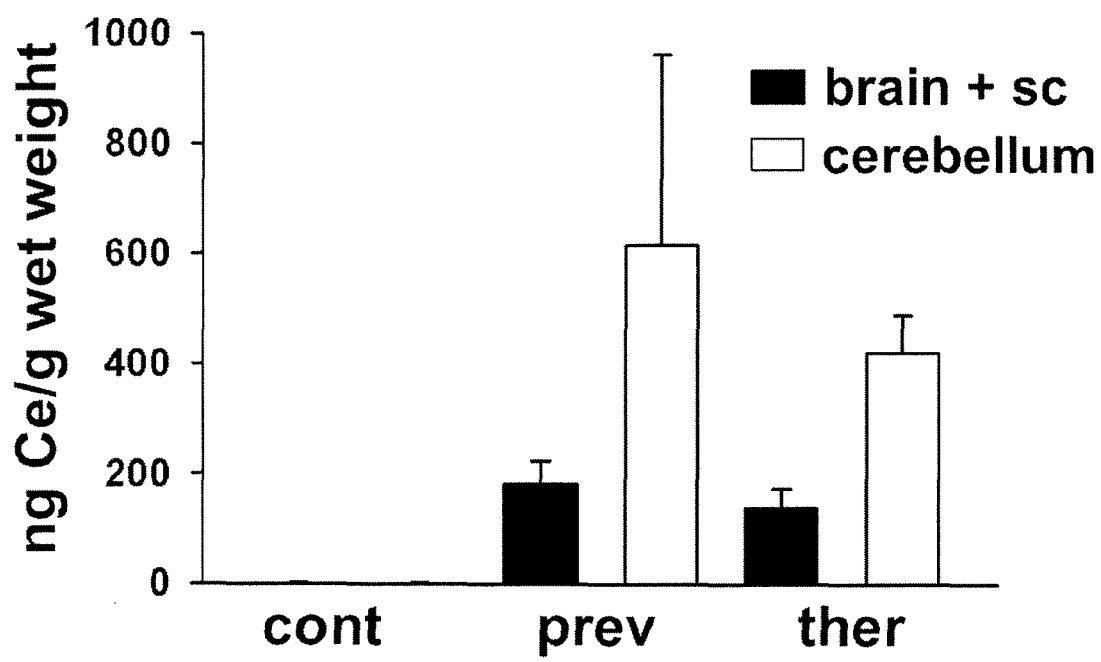
FIG. 23 is a chart of accumulated total ceria in the brain and spinal cord (sc) and in isolated cerebellum tissues taken from C57BL/6 mice induced with chronic-progressive MS and administered with vehicle control (cont) or with 20 mg/kg CeNPs in the preventative (prev) and therapeutic (ther) treatment regimens.
Figure 24:
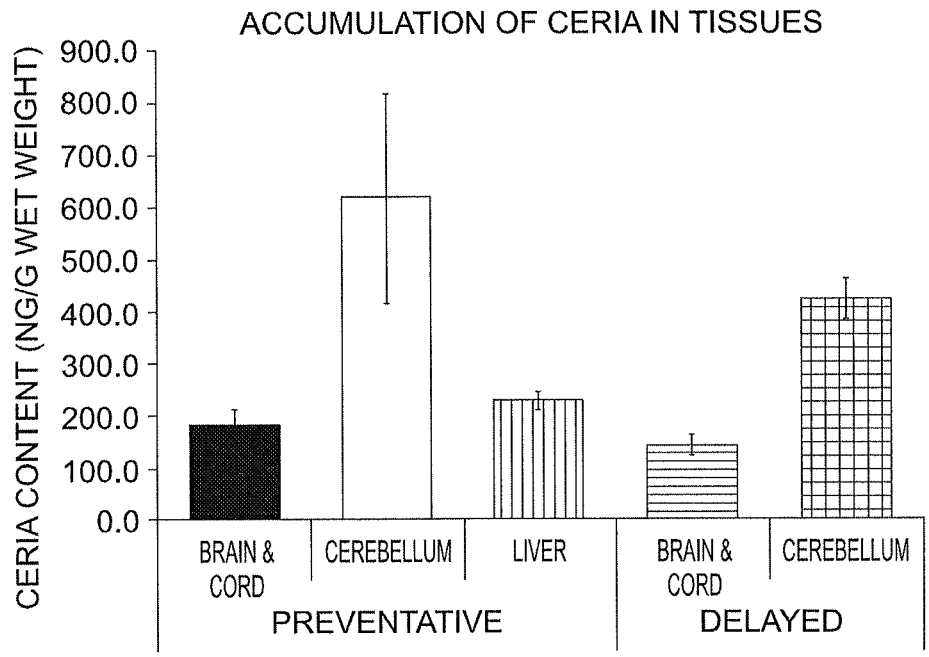
FIG. 24 is a chart of ICP-MS results for accumulation of ceria in various tissues taken from C57BL/6 mice induced with chronic-progressive MS and administered with 20 mg/kg CeNPs in the preventative and therapeutic treatment regimens, and sacrificed on Day 42 post disease induction.

Results of cerium content analysis by inductively coupled plasma mass spectrometry (ICP-MS) of organs and brain sections isolated from mice treated with CA/EDTA nanoceria are shown in FIGS. 23-24, indicating that cerium accumulated highest in the cerebellum for both the preventative and therapeutic treatment regimens.

Reactive oxygen species (ROS) levels were studied in brain slices prepared from the cerebellum of mice that were induced to developed EAE (chronic-progress symptoms of MS), the slices having been prepared 1 week after the final CA/EDTA nanoceria injection (n=12 mice). ROS levels were measured using the fluorescent probe CM-DFCDA (Invitrogen), using methods described in Estevez, A Y; et al., Neuroprotective mechanisms of cerium oxide nanoparticles in a mouse hippocampal brain slice model of ischemia, Free Radic. Biol. Med. (2011)51(6):1155-63 (doi:10.1016/j.radbiomed.2011.06.006).

Figure 25:
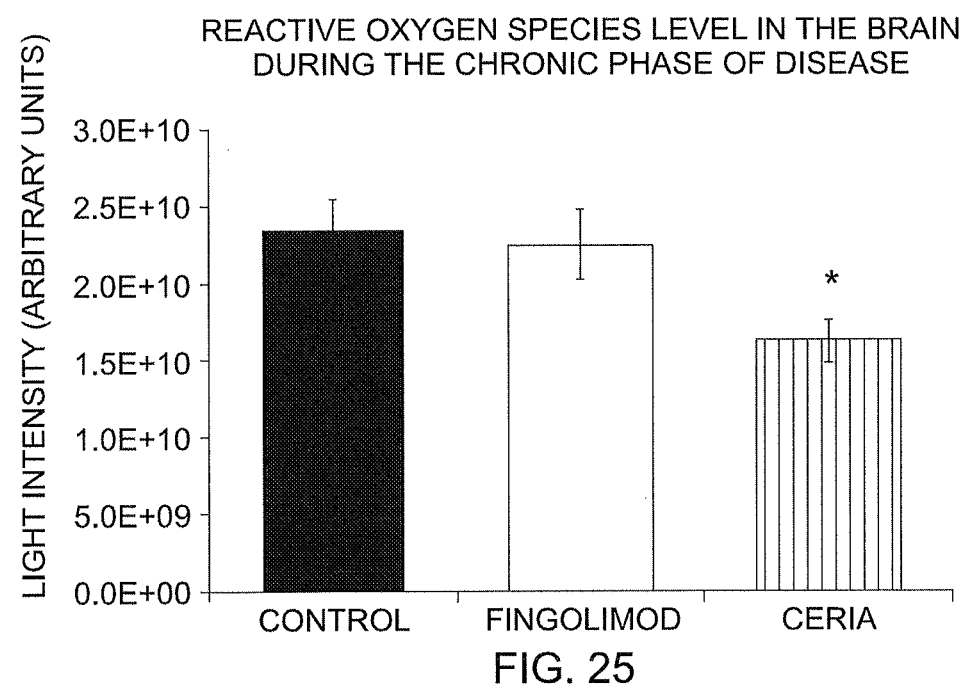
FIG. 25 is a chart of Reactive Oxygen Species Level (Light Intensity) in the brain (cerebellum sections) during the chronic phase (Day 42) of chronic-progressive MS for C57BL/6 mice treated with vehicle control, Fingolimod, and Ceria (CeNPs) administered by the preventative (30 mg/kg dosage) treatment regimen.
Figure 26:
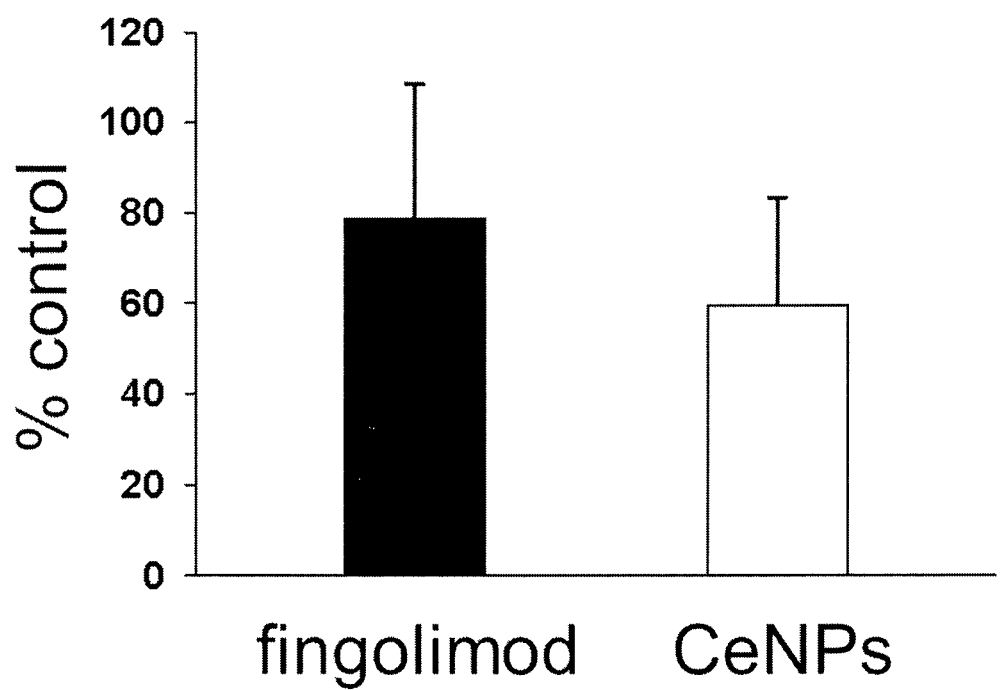
FIG. 26 is a chart of Reactive Oxygen Species Level (Light Intensity) in the brain (cerebellum sections) during the chronic phase (Day 42) of the chronic-progressive model of MS expressed as a percentage of the control for the Fingolimod and CeNPs administered by the preventative (30 mg/kg dosage) treatment regimens.

Intracellular ROS levels decreased significantly in brain slices from CA/EDTA nanoceria treated mice compared to control and to fingolimod treated animals, when tested 7 days after last drug treatment (FIGS. 25-26).

Figure 27:
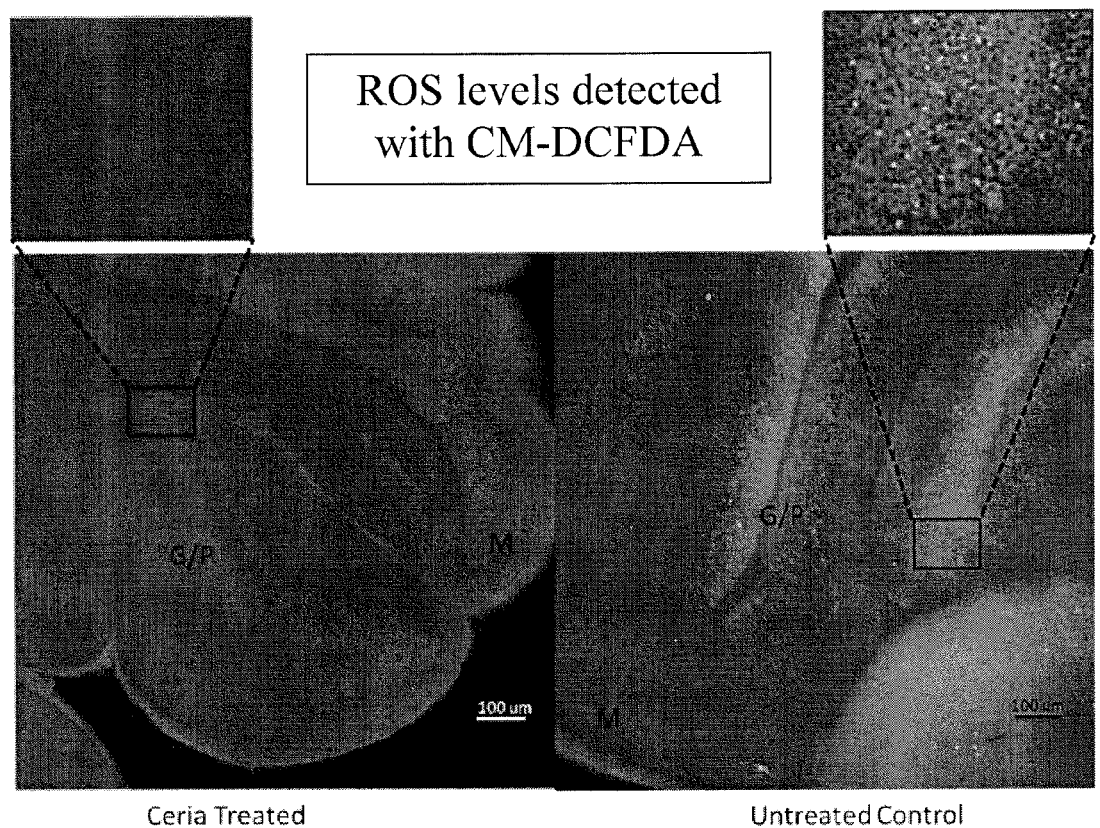
FIG. 27 contains fluorescence microscopy images of cerebellum brain slices treated with free radical indicator dye CM-DCFDA taken on Day 42 from Ceria (CeNPs) treated (preventative treatment regimen) and Untreated Control mice (pseudo-colored images such that higher fluorescence intensity appears as a warmer (e.g. red/orange, lighter areas) color and lower intensity appears as a cooler (e.g. blue/violet, darker areas) color).
Figure 28:
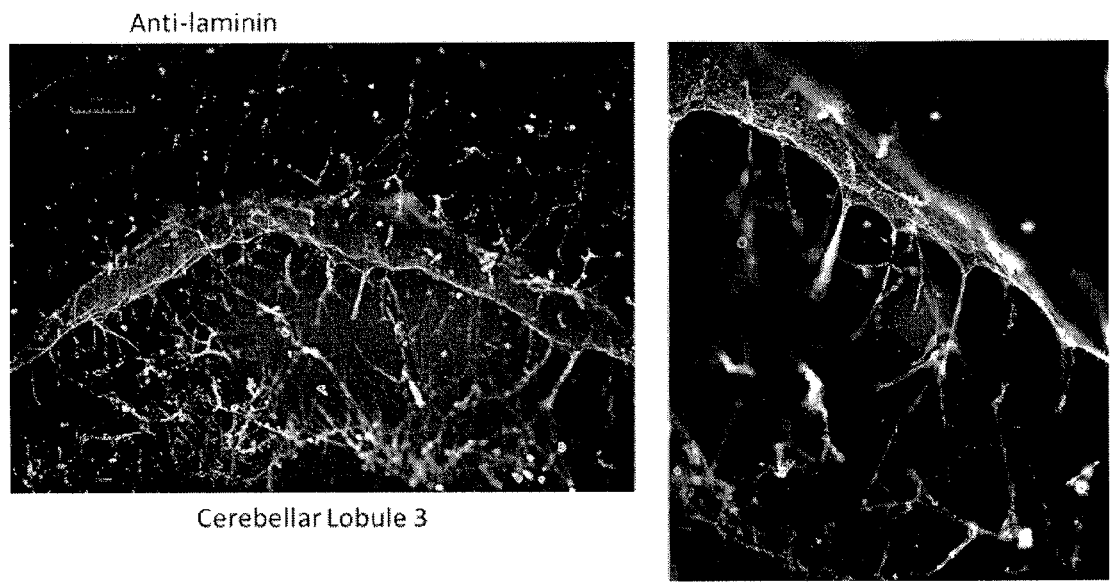
FIG. 28 contains microscopy images of mouse cerebellum brain slices treated with immunohistochemical stain.

Broad and uniform distribution of nanoceria into the brain parenchyma tissues of a living mammal, when imaged at a micron or submicron resolution, has not been previously reported. To this end, the broad distribution of CA/EDTA nanoceria particles throughout the mouse brain tissue is indicated by the diffuse and uniform nature of the decreased ROS fluorescence (CM-DFCDA) levels evident in cerebellar slices taken from a CA/EDTA nanoceria treated and untreated paired control (FIG. 27). In particular, it was noted that the distribution of fluorescence in the nanoceria treated slice (FIG. 27) does not correspond to the distribution of cerebellar microvasculature depicted at a similar scale of magnification in FIG. 28, suggesting that the CA/EDTA nanoceria particles are not limited to the microvascular vessels or trapped in the Blood Brain Barrier cells, but are broadly distributed throughout the cerebellar tissue. These observations are consistent with the penetration of CA/EDTA nanoceria particles through the compromised blood brain barrier of EAE mice induced with chronic-progressive multiple sclerosis, and that the particles were widely dispersed in the brain tissues.

Relapse/Remitting Multiple Sclerosis
Murine EAE Model of Multiple Sclerosis

Many of the pathological features of the onset of MS are modeled by the murine experimental autoimmune encephalomyelitis (EAE) model, wherein an inflammatory disorder is induced by immunization with myelin antigens. The EAE model is characterized by blood-brain-barrier (BBB) breakdown, perivascular infiltration of immune cells, microglia activation, and demyelination. The EAE model has been critical in the development of current therapies used in the treatment of MS.

Female SJL-EAE mice were treated with vehicle, vehicle plus CA/EDTA ceria nanoparticles or vehicle plus commercial nanoceria obtained from Sigma-Aldrich or Alfa Aesar. Commercially obtained nanoceria was dispersed in vehicle with sonication just prior to use. In the Preventative dosing design, the mice were IV tail vein injected with 10 mg/kg of the CA/EDTA ceria nanoparticles on the day prior to disease induction and on the day of disease induction, followed by injections of 6 mg/kg of the CA/EDTA ceria nanoparticles on Days 3, 7, 14 and 21 post disease induction. The Therapeutic dosing design was similar except that the first two injections (prior to and day of disease induction) were eliminated. The CA/EDTA ceria nanoparticles were mixed in PBS/50 mM sodium citrate saline vehicle prior to administration.

The mice were induced with experimental autoimmune encephalomyelitis (EAE), i.e. relapse/remitting multiple sclerosis-like symptoms, as follows: a 0.1 ml intravenous tail injection of 200 µg myelin basic protein peptide (PLP139-151) dissolved in phosphate buffered saline (PBS) mixed with an equal volume of complete Freund's adjuvant, was followed by an 0.1 ml intraperitoneal injections of 200 ng pertussis toxin in PBS on Day 0 and Day 2.

Following disease induction, mice developed the first episode of paralysis 11-14 days (peaked at 14 days) after immunization and, similar to most human MS patients, they fully or almost fully recovered from this first wave of paralysis by about Day 20.

Testing included daily clinical scoring along with the three motor behavior tests designed to evaluate cerebellar function (Balance Beam), forelimb strength (Hanging Wire), and hindlimb strength (Rotarod), as described previously.

Figure 29:
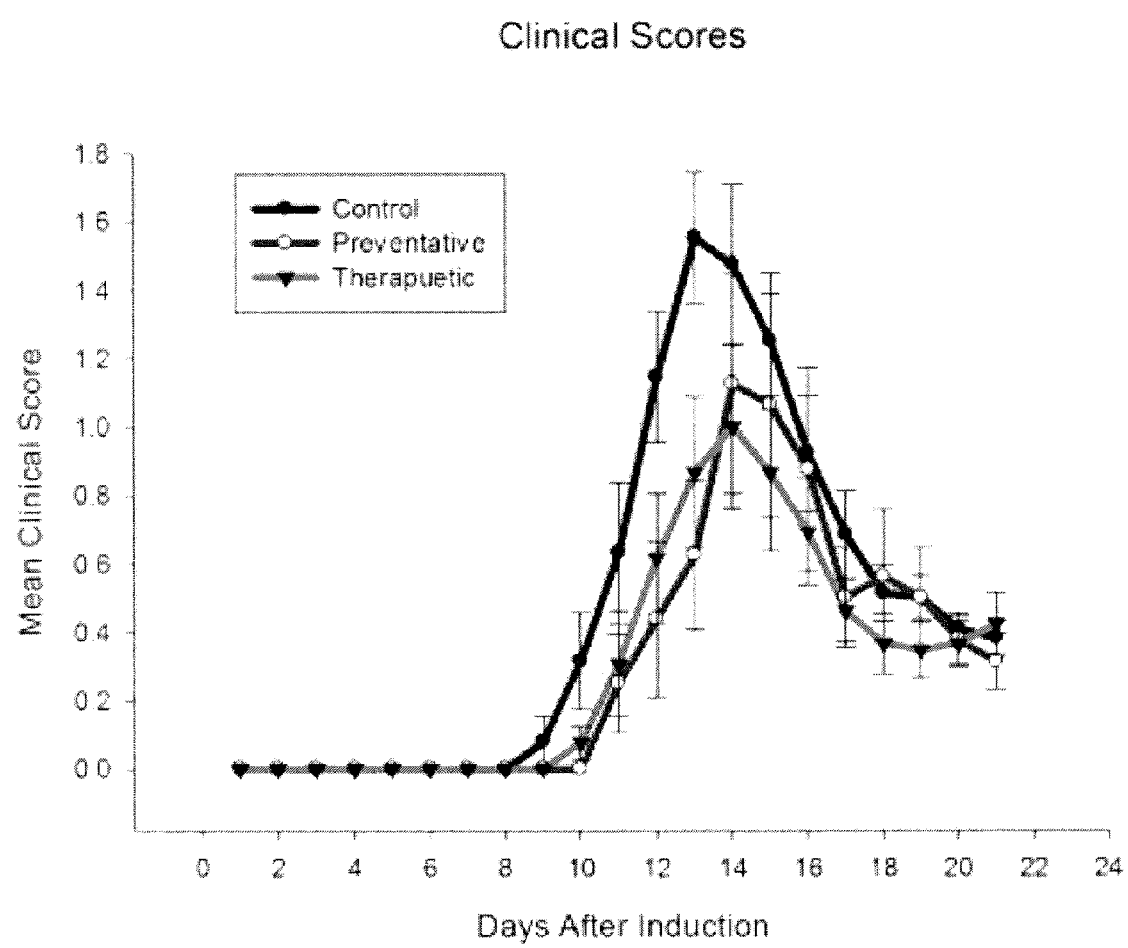
FIG. 29 is a plot of Mean Clinical Score as a function of time for the relapse/remitting model of MS for vehicle control and for CeNPs administered in the preventative and therapeutic treatment regimens.
Figure 30:
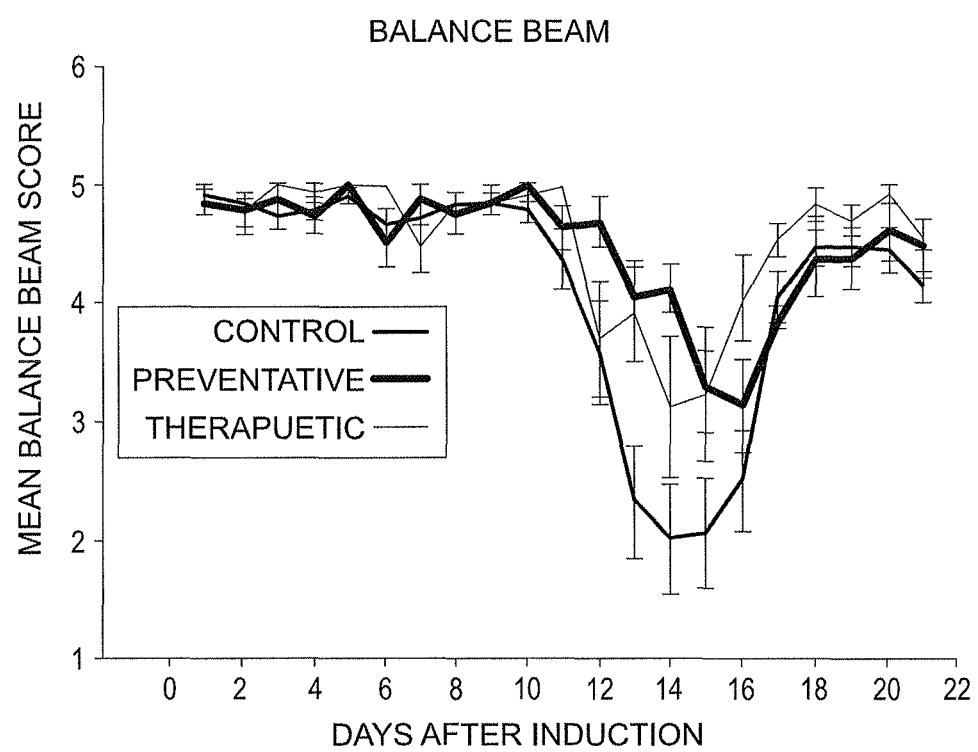
FIG. 30 is a plot of Balance Beam Test performance as a function of time for the relapse/remitting model of MS for the control and for CeNPs administered by the preventative and therapeutic treatment regimens.
Figure 31:
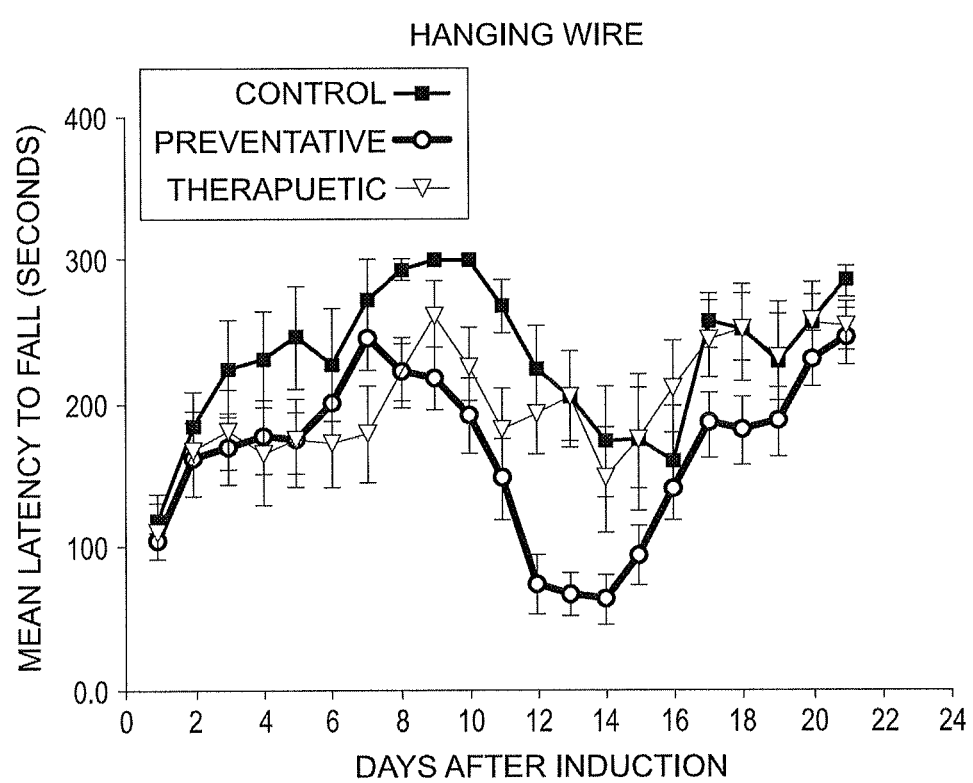
FIG. 31 is a plot of Hanging Wire Test performance as a function of time for the relapse/remitting model of MS for the control and for CeNPs administered by the preventative and therapeutic treatment regimens.
Figure 32:
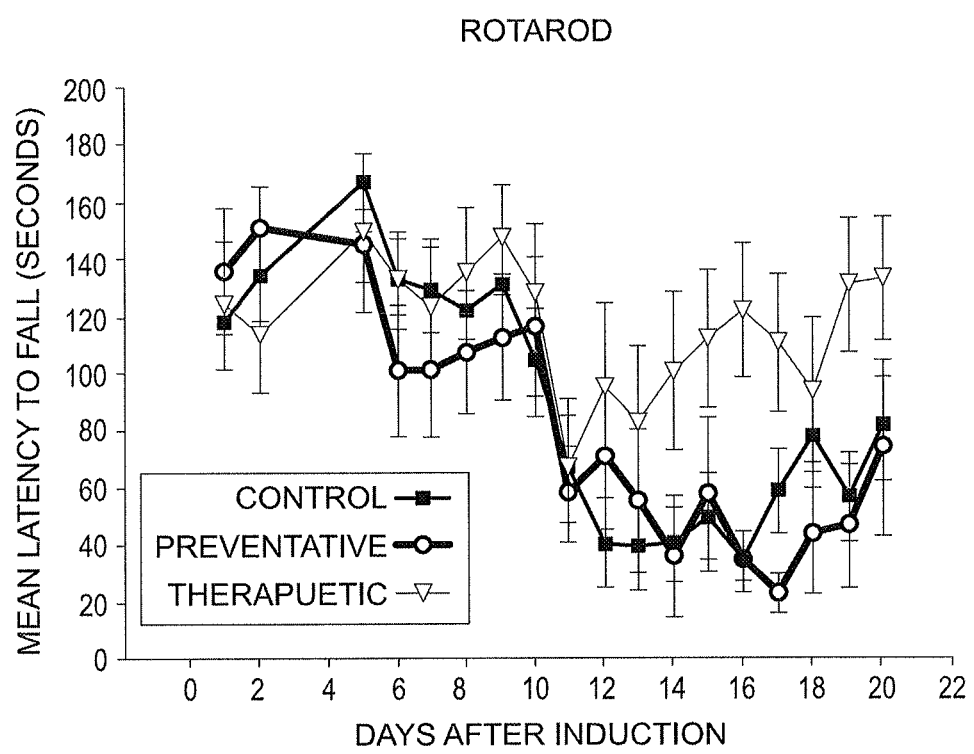
FIG. 32 is a plot of Rotorod Test performance as a function of time for the relapse/remitting model of MS for the control and for CeNPs administered by the preventative and therapeutic treatment regimens.
Figure 33:
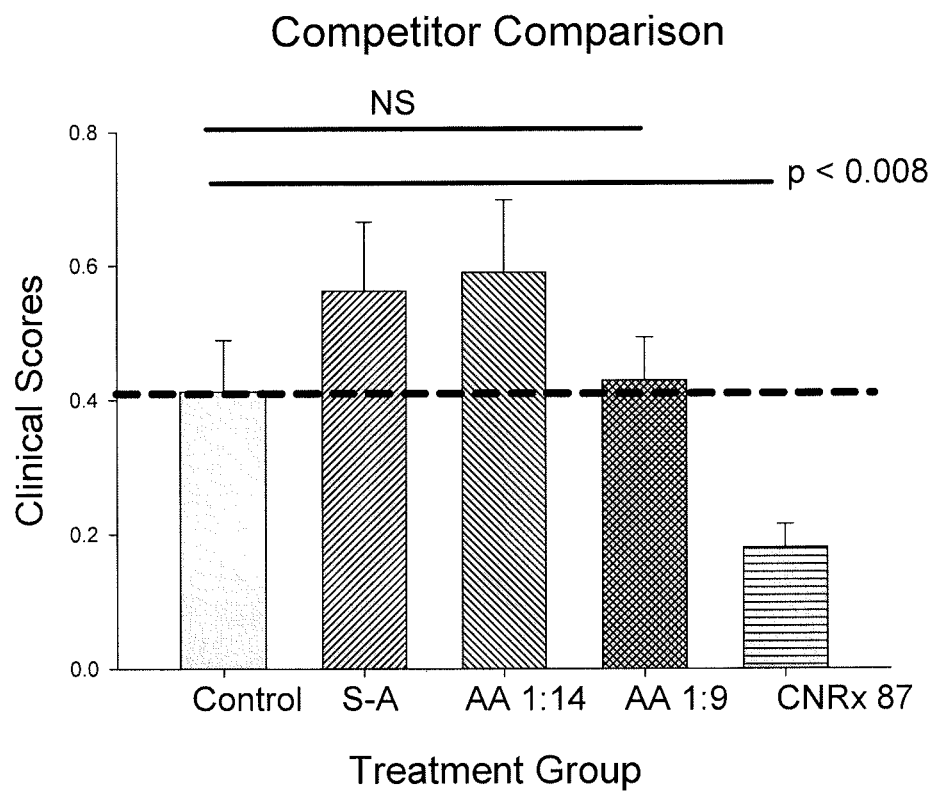
FIG. 33 is a chart of Clinical Scores (AUC) over the disease course for the relapse/remitting model of MS for the Control, Sigma-Aldrich, Alfa Aesar (1:14 and 1:9 dilutions) and for CA/EDTA ceria nanoparticles (CNRx 87) administered by the therapeutic treatment regimen.

In regard to onset of the disease, a substantial delay (improvement) was seen in the following tests: Clinical Scoring results for both the Preventative and Therapeutic dosing designs (FIG. 29), Balance Beam results for the Preventative dosing design (FIG. 30), and in the Hanging Wire results for both the Preventative and Therapeutic dosing designs (FIG. 31).

A statistical summary of the quantitative (average) effects of the CA/EDTA ceria nanoparticles administered by the Preventative and Therapeutic dosing designs compared to vehicle controls is tabulated in Table 6. Statistically significant improvements were shown for Clinical Scoring and each of the motor behavior tests for both Preventative and Therapeutic dosing designs, except for the case of the Preventative dosing design for the Rota rod test.

TABLE 6

| PLP Model | Peak Clinical Scores | Rotorod Max Latency to Fall | Hanging Wire Max Latency to Fall | Balance Beam Score |
|---|---|---|---|---|
| Control (n = 20) vs Preventative (n = 8) | $\bar{X}$ 1.7 ± 0.2 SE $\bar{X}$ 0.9 ± 0.3 SE p = 0.048 | $\bar{X}$ 33.8 ± 10 SE $\bar{X}$ 27.1 ± 5.6 SE p = 0.799 | $\bar{X}$ 63.3 ± 17 SE $\bar{X}$ 158.7 ± 39 SE p = 0.001* | $\bar{X}$ 1.8 ± 0.4 SE $\bar{X}$ 4.1 ± 0.58 SE p = 0.005* |
| Control (n = 20) vs Therapeutic (n = 12) | $\bar{X}$ 1.7 ± 0.2 SE $\bar{X}$ 0.9 ± 0.25 SE p = 0.038* | $\bar{X}$ 33.8 ± 10 SE $\bar{X}$ 100.8 ± 16 SD p = 0.003* | $\bar{X}$ 63.3 ± 17 SE $\bar{X}$ 146.6 ± 37 SE p = 0.001* | $\bar{X}$ 1.8 ± 0.4 SE $\bar{X}$ 3.1 ± 0.63 SE p = 0.005* |

Figure 3:
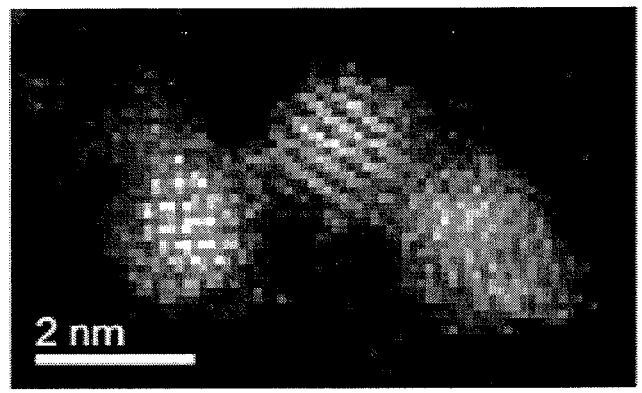
FIG. 3 is a high resolution TEM micrograph of dried down CA/EDTA ceria nanoparticles.
Figure 4:
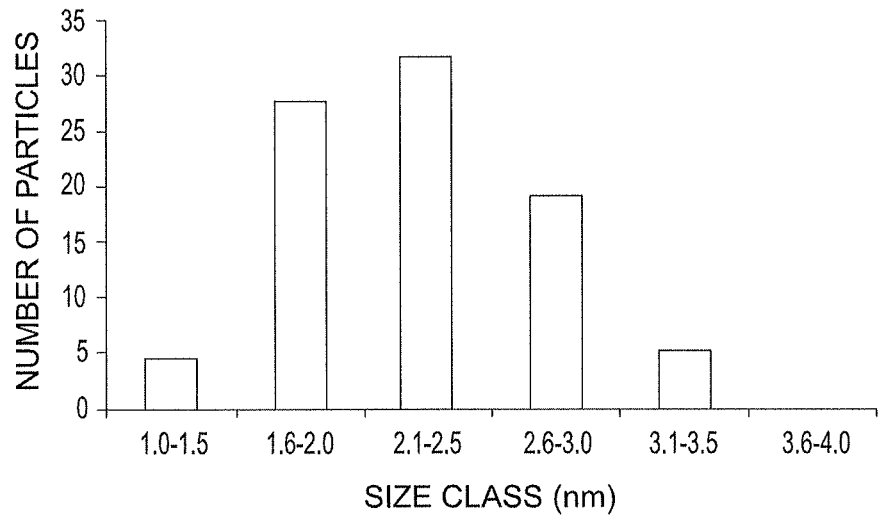
FIG. 4 is a size class distribution chart of the CA/EDTA ceria nanoparticles.

Comparison of the average Clinical Scores (AUC) over the disease course for the relapse/remitting model of MS indicates that relative to the Control, only the CA/EDTA ceria nanoparticles (CNRx 87) ameliorate the disease (FIG. 3). Results for Sigma-Aldrich and Alfa Aesar (1:14 and 1:9 dilutions) comparisons are either worse or no different from the Control.

Figure 34:
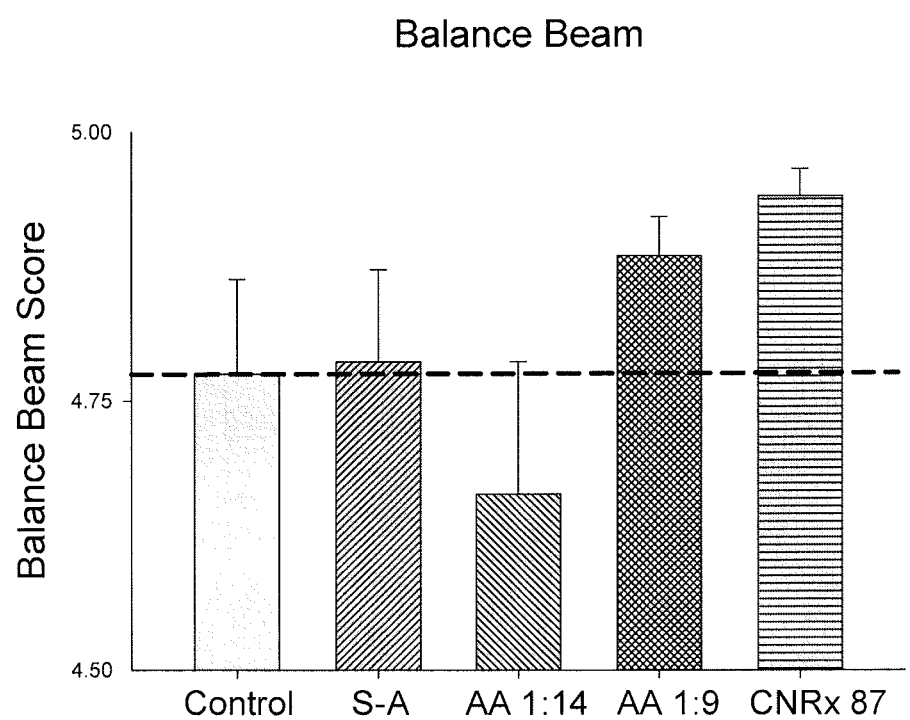
FIG. 34 is a chart of Average Balance Beam Score over the disease course for the relapse/remitting model of MS for the Control, Sigma-Aldrich, Alfa Aesar (1:14 and 1:9 dilutions) and for CA/EDTA ceria nanoparticles (CNRx 87) administered by the therapeutic treatment regimen

Comparison of the average Balance Beam Score over the disease course for the relapse/remitting model of MS indicates that the CA/EDTA ceria nanoparticles (CNRx 87) performed the best, whereas, with the exception of the Alfa Aesar 1:9 dilution, comparisons were either worse or no different from the Control (FIG. 34).

Figure 35:
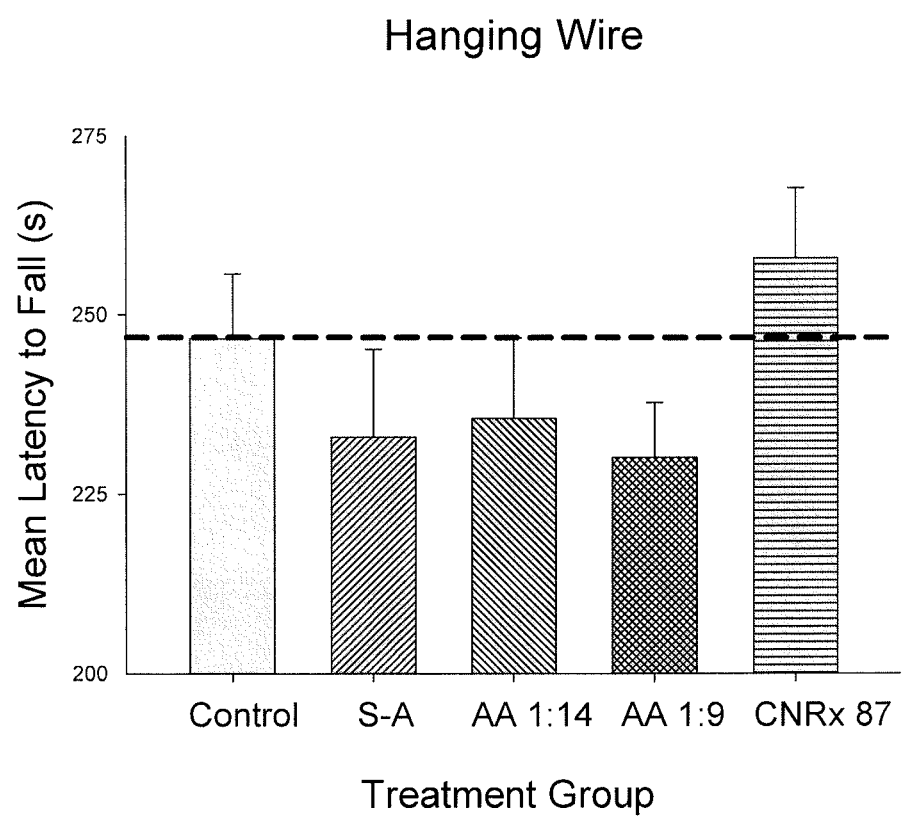
FIG. 35 is a chart of Average Hanging Wire Test performance over the disease course for the relapse/remitting model of MS for the Control, Sigma-Aldrich, Alfa Aesar (1:14 and 1:9 dilutions) and for CA/EDTA ceria nanoparticles (CNRx 87) administered by the therapeutic treatment regimen

Comparison of the average Hanging Wire Test results over the disease course for the relapse/remitting model of MS indicates that relative to the Control, only the CA/EDTA ceria nanoparticles (CNRx 87) ameliorate the disease by increasing the mean latency time to fall (FIG. 35). Results for Sigma-Aldrich and Alfa Aesar (1:14 and 1:9 dilutions) comparisons are either worse or no different from the Control.

Figure 36:
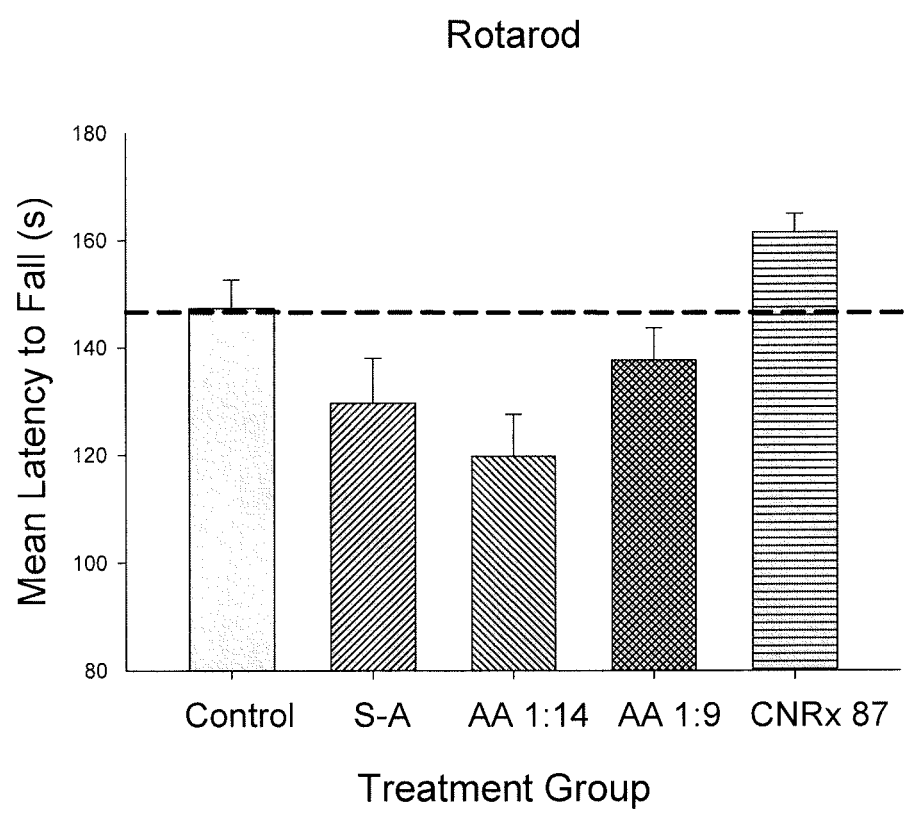
FIG. 36 is a chart of Average Rotarod Test performance over the disease course for the relapse/remitting model of MS for the Control, Sigma-Aldrich, Alfa Aesar (1:14 and 1:9 dilutions) and for CA/EDTA ceria nanoparticles (CNRx 87) administered by the therapeutic treatment regimen

Comparison of the average Rotarod Test results over the disease course for the relapse/remitting model of MS indicates that relative to the Control, only the CA/EDTA ceria nanoparticles (CNRx 87) ameliorate the disease by increasing the mean latency time to fall (FIG. 36). Results for Sigma-Aldrich and Alfa Aesar (1:14 and 1:9 dilutions) comparisons are worse than the Control.

Comparison of Cerium Brain Levels

Using the Therapeutic dosing design, EAE-induced mice (n=12) received tail vein injections of ceria dispersions (24 mg/kg total dosage) comprising the CA/EDTA ceria nanoparticles or a commercially available nanoceria (i.e. obtained from Sigma-Aldrich and Alfa Aesar). Twenty four hours after the last injection, the brains and other organs were harvested and concentration of ceria in these organs was determined using inductively coupled plasma mass spectroscopy (ICP-MS).

Figure 37:
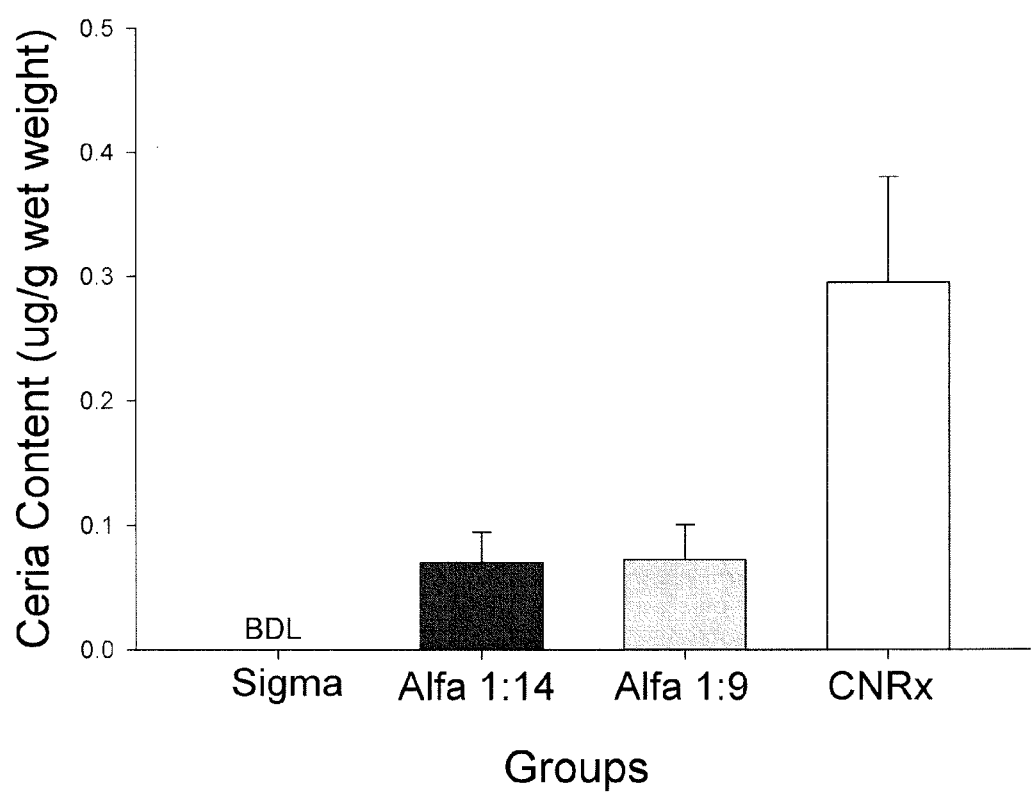
FIG. 37 is a chart of brain deposition results for the relapse/remitting model of MS dosed by the therapeutic treatment regimen with CA/EDTA ceria nanoparticles (labeled CNRx) compared to various commercially available nanoceria (24 mg/kg total dosage).

Brain deposition results shown in FIG. 37 indicate that cerium was below the detection limit for Sigma-Aldrich nanoceria, whereas the deposition in the brain of CNRx nanoceria embodiment of the invention is about 4 times greater than that of the Alfa Aesar materials.

In a separate biodistribution study, four adult SJL mice between the ages of 1-3 months possessing the experimental autoimmune encephalomyelitis (EAE) characteristic, were tail vein injected with 52 mg of CA/EDTA nanoceria per kg of mouse body mass (52 mg/kg dosage) in saline at three time points: Day 0, Day 3 and Day 7. In addition, two of these mice were induced to develop multiple sclerosis (MS) like symptoms (experimental autoimmune encephalomyelitis) by injection of proteolipid protein (PLP) on Day 0, and demonstrated peak, MS-like symptoms by Day 7. The other two mice were not induced to develop MS-like symptoms, but were simply injected with saline as a vehicle control. On Day 8 (24 hours after the last injection of nanoceria) each of the four animals was sacrificed; and their heart, kidney, liver, lung, spleen, brain and spinal cord organs removed, frozen and submitted for cerium content analysis.

The organs were analyzed for bulk cerium content using inductively coupled plasma mass spectrometry (ICP-MS) by the following procedures. A 0.1-0.5 g tissue sample of each of the organs was digested with 1 ml of optima $HNO_3$ in a 15 ml polypropylene tube, and heated to 105° C. for 30 minutes in a microwave digestion oven. The sample was allowed to cool, 100 µl of $H_2O_2$ added and the sample diluted to 10 ml final volume with deionized water. These digested samples were analyzed for bulk cerium content by ICP-MS (7500cx, Agilent, Santa Clara, Calif.) operated in normal mode. The instrument was calibrated with NIST-traceable primary standards and a second source standard was used as a calibration check.

Table 5 shown below contains the bulk cerium content results for the four mice (labeled Mouse 1-4) that constitute the biodistribution study described herein as embodiments of the invention. In addition, the results of earlier whole animal (rodent) biodistribution studies of intravenously administered nanoceria reported Yokel et al. Nanotoxicology 3(3), 234-248 (2009) (data taken from Table I therein), and Hardas et al. Toxicological Sciences 116(2), 562-576 (2010) (data taken for 20-h termination from Table 2 therein), are included for comparison.

TABLE 5

| Study | Dosage (mg/kg) | Induced MS | Bulk Cerium Content (mg/kg) | | | | |
|---|---|---|---|---|---|---|---|
| | | | Brain | Heart | Kidney | Liver | Lung | Spleen |
| Yokel et al. | 50 | | 1 | — | — | 610 | — | 2828 |
| Hardas et al. | 100 | | 0.6 | — | — | 1007 | — | 2885 |
| Mouse 1 | 52 | Yes | 28 | 767 | 3798 | 30028 | 1316 | 17762 |
| Mouse 2 | 52 | Yes | 42 | 1304 | 6985 | 31609 | 1419 | 17090 |
| Mouse 3 | 52 | No | 70 | 1325 | 3343 | 26141 | 1807 | 18814 |
| Mouse 4 | 52 | No | 59 | 1241 | 4431 | 25567 | 6303 | 21655 |

Comparison of the bulk cerium content between the studies described herein (Mouse 1-4) and the earlier studies done at comparable or higher dosage (Yokel et al. and Hardas et al.) indicates that about 30-100 times more cerium is associated with the brain, about 25-50 times more cerium is associated with the liver, and about 7 times more cerium is associated with the spleen as a result of injecting the aqueous dispersion of 2.5 nm diameter CA/EDTA ceria nanoparticles described herein as an embodiment of the invention. In addition, it is noted that the surprisingly large increase in the amounts of cerium associated with the various organs was observed in both healthy mice (Mouse 3-4) that possess a fully intact BBB, as well as in the mice with induced MS-like symptoms (Mouse 1-2) that are expected to have a substantially compromised BBB.

It is noted that differences among in the biodistribution protocols employed in the studies described herein (Mouse 1-4) and the earlier studies done at comparable or higher dosage (Yokel et al. and Hardas et al.) were, in general, quite small in comparison to the large increases in cerium associated with the various target organs as a result of this embodiment of the invention. Specifically, Yokel et al. used a 50 mg/kg dose and terminated the animals 20 hours after the final injection. Hardas et al. used a 100 mg/kg dose and also terminated the animals 20 hours after the final injection, and the inventors herein used a 52 mg/kg dose and terminated the animals 24 hours after the final injection.

Bio-Persistence Studies

Figure 38:
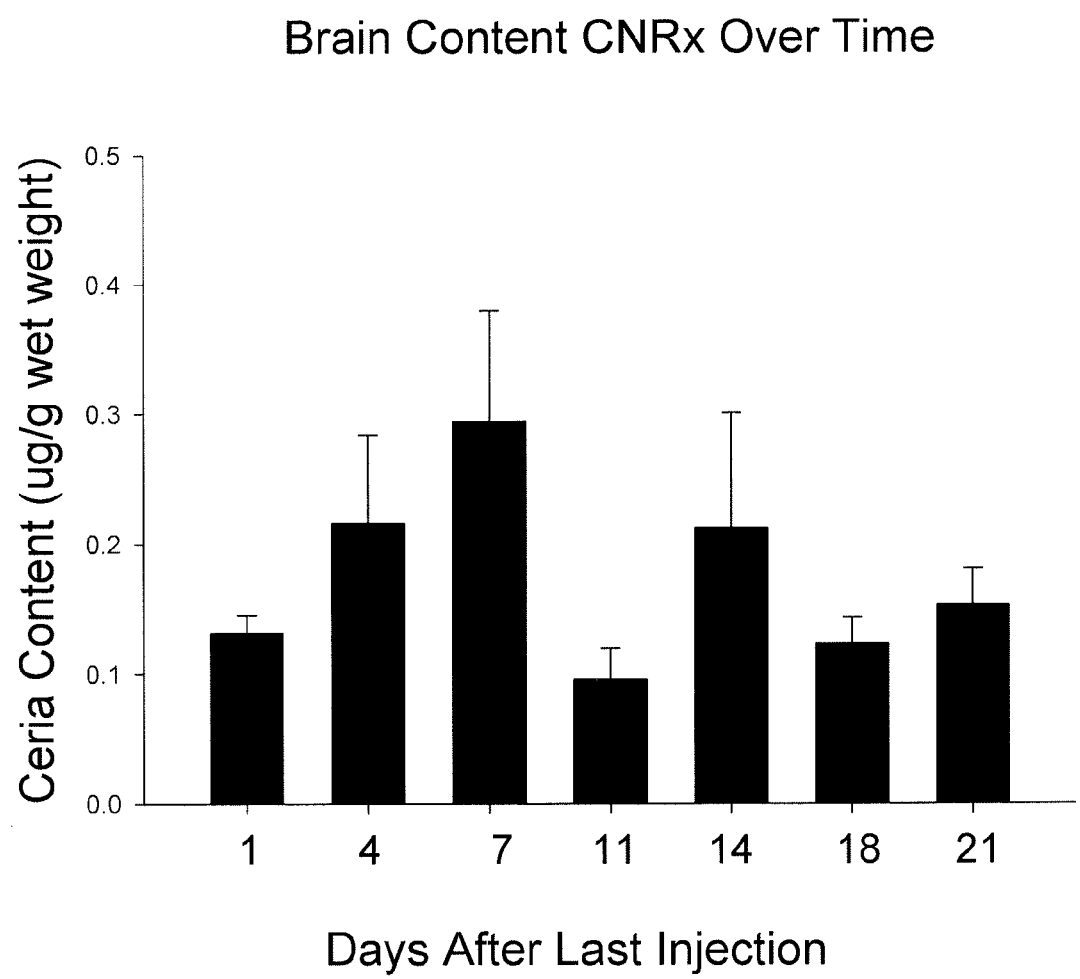
FIG. 38 is a chart of brain ceria content as a function of time following the final injection of CA/EDTA ceria nanoparticles in the relapse/remitting model of MS (24 mg/kg total dosage).

At different time points (1-21 days) from the last CA/EDTA ceria nanoparticle injection (24 mg/kg total dosage), brains of mice induced with the relapse/remitting form of EAE-(n=22) were harvested and the concentration of cerium determined using ICP-MS. Significant levels of ceria were detectable up until at least 3 weeks after the last injection (FIG. 38).

Figure 39:
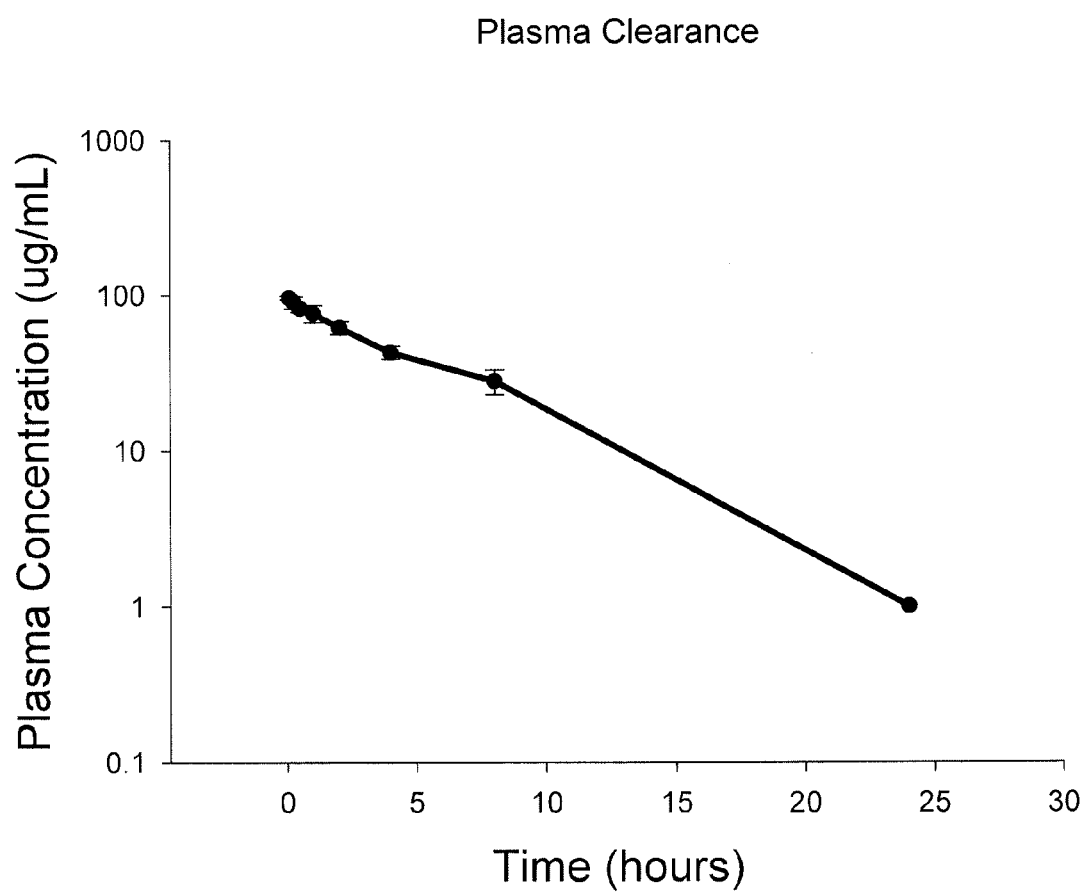
FIG. 39 is a plot of ceria concentration in the blood plasma over a 24 hour period for a 10 mg/kg intravenous (IV) injection and for a 50 mg/kg subcutaneous injection of CeNPs into rats.

From studies done in rats, following a single 10 mg/kg intravenous injection or a single 50 mg/kg subcutaneous injection, measurements of cerium content in the blood of the rats indicate that CA/EDTA ceria nanoparticles were cleared quickly from the blood plasma (FIG. 39).

Toxicity Studies

No genotoxicity was observed for the CA/EDAT ceria nanoparticle embodiment when evaluated by the Green-Screen assay of Gentronix Ltd. (UK).

No phospholipidosis toxicity was observed for the CA/EDAT ceria nanoparticle embodiment when evaluated by the Phospholipidosis (PLD) assay of Gentronix Ltd. (UK).

No potassium channel interference was observed for the CA/EDAT ceria nanoparticle embodiment when evaluated by the hERG-450 assay of Gentronix Ltd. (UK).

Amyotrophic Lateral Sclerosis

Amyotrophic Lateral Sclerosis (ALS) is progressive, fatal, motor neuron disease caused by the degeneration of upper and lower neurons located in the ventral horn of the spinal cord and the cortical neurons that provide their efferent input. The condition is often referred to as Lou Gehrig's disease, after the baseball player who was diagnosed with the disease in 1939.

While the cause of ALS is not known, the discovery that familial ALS is related to mutations in the gene that produces Cu/Zn superoxide dismutase enzyme (SOD1), a powerful antioxidant, suggests that accumulation of free radical may be involved. However, mice lacking the SOD1 gene do not customarily develop familial ALS, rather they exhibit an increase in age-related muscle atrophy (sarcopenia).

$SOD1^{G93A}$ mice obtained from Jackson Laboratory (Bar Harbor, Me., USA; strain B6SJL-TgSOD1$^{G93A}$) underwent weekly clinical and motor behavior testing (described above) and were randomized into treatment groups at disease onset. One group of mice received saline vehicle control injections alone, whereas the nanoceria treated animals were given tail vein injections of CA/EDTA ceria nanoparticles of 16 mg/kg either once or twice per week.

Figure 40:
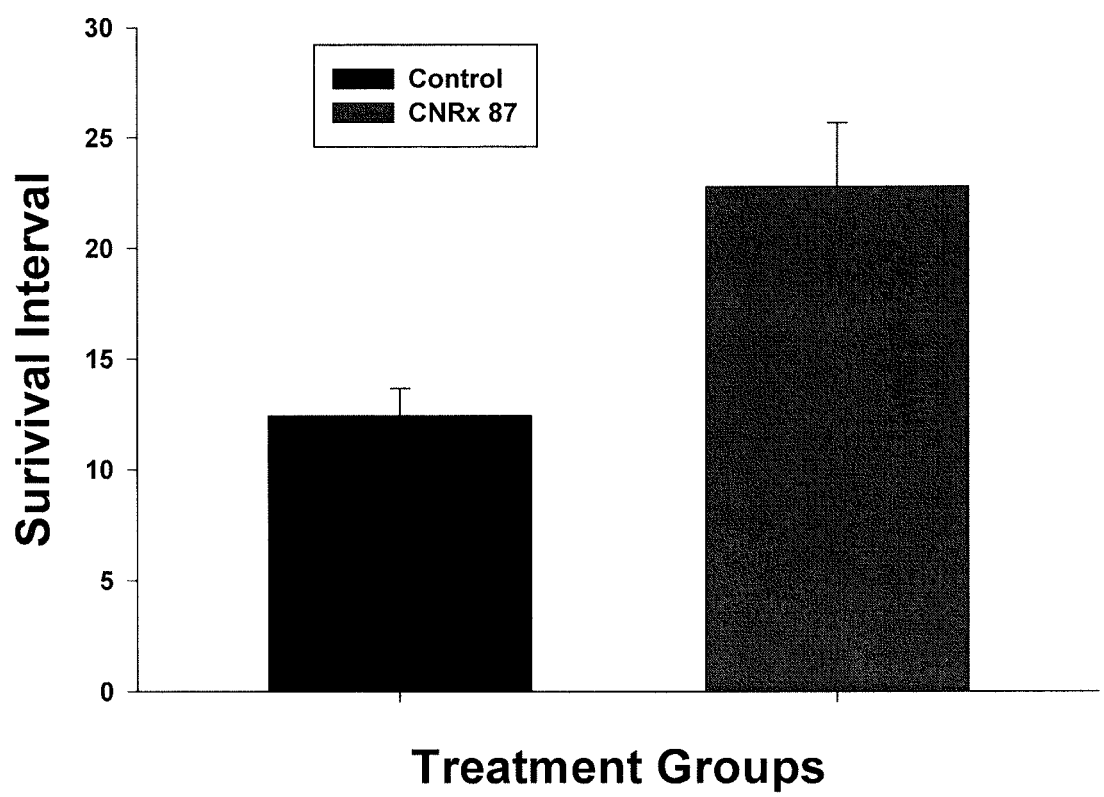
FIG. 40 is a chart of Survival Interval (days) for G93A model ALS mice treated with vehicle control and CeNPs (CNRx 87).

Male G93A mice receiving the nanoceria treatment displayed very substantial improvements in all motor skill tests (Hanging Wire, Balance Beam and Rotarod). An extension in lifespan relative to the control, shown in FIG. 40, was also exhibited by the male G93A mice receiving the CA/EDTA ceria nanoparticle treatment.

Ischemic Reperfusion Injury

Reperfusion injury refers to the tissue damage that occurs when blood supply returns to the tissue after a period of ischemia. The absence of oxygen and nutrients from the blood during the ischemic period creates a condition wherein the restoration of circulation results in inflammation and oxidative damage through the induction of oxidative stress rather than the restoration of normal metabolic function.

The inflammatory response is believed to partially mediate the damage of reperfusion injury. White blood cells carried to the area by newly returning blood may release a variety of inflammatory factors, including interleukins and free radicals.

Figure 41:
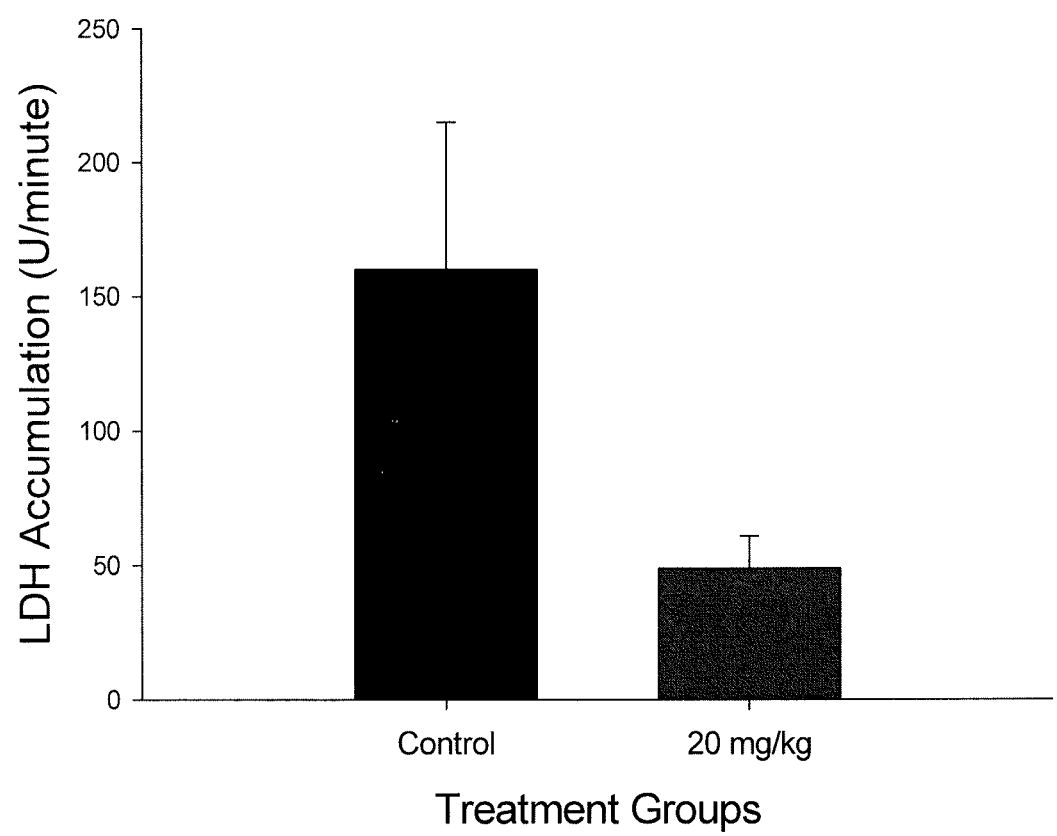
FIG. 41 is a chart of LDH accumulation following myocardial ischemia/reperfusion via the Langendorff hanging heart procedure for mice treated with vehicle control and with CeNPs (CNRx 87) dosed at 20 mg/kg on Days −4, −2 and 0.

In a demonstration of murine cardiac ischemic reperfusion injury, mice were injected with vehicle or CA/EDTA ceria nanoparticles at a 20 mg/kg dosage on Days −4 and −2 via the jugular vein. On Day 0 hearts were excised and perfused on a Langendorff system. Necrotic cell death was monitored by lactate dehydrogenase (LDH) assay, following 25 min of global no-flow ischemia and a 45 min reperfusion. FIG. 41 shows an improvement in the form of a reduction in LDH accumulation for the CA/EDTA ceria nanoparticle treatment relative to the vehicle control. Assessment of cardiac infarct size also suggested a protective effect was provided by the 20 mg/kg dose of CA/EDTA ceria nanoparticles.

What is claimed:

1. A pharmaceutical composition for the treatment of a patient suffering from a disease associated with oxidative stress comprising a therapeutically effective amount of a dispersion of cerium-containing nanoparticles and optionally a pharmaceutically acceptable excipient, wherein the cerium-containing nanoparticles are stabilized by citric acid and ethylenediaminetetraacetic acid.

2. A nanoparticle dispersion comprising cerium-containing nanoparticles stabilized by citric acid and ethylenediaminetetraacetic acid.

3. The pharmaceutical composition according to claim 1, wherein greater than about 95% of the cerium-containing nanoparticles are non-agglomerated.

4. The nanoparticle dispersion according to claim 2, wherein greater than about 95% of the cerium-containing nanoparticles are non-agglomerated.

5. The pharmaceutical composition according to claim 1, wherein said dispersion of cerium-containing nanoparticles has a zeta-potential ranging from about −15 mV to about −30 mV.

6. The nanoparticle dispersion according to claim 2, wherein said dispersion of cerium-containing nanoparticles has a zeta-potential ranging from about −15 mV to about −30 mV.

7. The pharmaceutical composition according to claim 1, wherein the citric acid and ethylenediaminetetraacetic acid are present in a molar ratio ranging from about 3.0 to about 0.1.

8. The nanoparticle dispersion according to claim 2, wherein the citric acid and ethylenediaminetetraacetic acid are present in a molar ratio ranging from about 3.0 to about 0.1.

9. The pharmaceutical composition according to claim 1, wherein the cerium-containing nanoparticles have a hydrodynamic diameter of 10 nm or less.

10. The nanoparticle dispersion according to claim 2, wherein the cerium-containing nanoparticles have a hydrodynamic diameter of 10 nm or less.

* * * * *